(12) United States Patent
Binkley et al.

(10) Patent No.: US 8,131,043 B2
(45) Date of Patent: Mar. 6, 2012

(54) METHOD AND APPARATUS FOR DETECTING INTERVENTRICULAR DYSSYNCHRONY

(75) Inventors: Philip F. Binkley, Upper Arlington, OH (US); Subha V. Raman, Columbus, OH (US)

(73) Assignee: The Ohio State University, Columbus, OH (US)

( * ) Notice: Subject to any disclaimer, the term of this patent is extended or adjusted under 35 U.S.C. 154(b) by 997 days.

(21) Appl. No.: 12/067,092

(22) PCT Filed: Sep. 18, 2006

(86) PCT No.: PCT/US2006/036384
§ 371 (c)(1),
(2), (4) Date: Mar. 17, 2008

(87) PCT Pub. No.: WO2007/035687
PCT Pub. Date: Mar. 29, 2007

(65) Prior Publication Data
US 2008/0253638 A1    Oct. 16, 2008

Related U.S. Application Data

(60) Provisional application No. 60/718,115, filed on Sep. 16, 2005.

(51) Int. Cl.
*G06K 9/00* (2006.01)
(52) U.S. Cl. ............................................. 382/131; 378/8
(58) Field of Classification Search .................. 382/128, 382/131; 378/8
See application file for complete search history.

(56) References Cited

U.S. PATENT DOCUMENTS

| | | | |
|---|---|---|---|
| 4,573,197 A | 2/1986 | Crimmins | |
| 5,107,838 A | 4/1992 | Yamaguchi | |
| 5,435,310 A | 7/1995 | Sheehan et al. | |
| 5,622,174 A * | 4/1997 | Yamazaki | 600/441 |

(Continued)

FOREIGN PATENT DOCUMENTS

EP    1102199 A2    5/2001

(Continued)

OTHER PUBLICATIONS

Ng et al., Prognostic implications of left ventricular dyssynchrony early after non-ST elevation myocardial infarction without congestive heart failure, Clincal research, European Heart Journal, 2009, pp. 298-308.*

(Continued)

*Primary Examiner* — Alexander H Taningco
(74) *Attorney, Agent, or Firm* — Calfee, Halter & Griswold LLP

(57) ABSTRACT

Several embodiments of a method and apparatus for detecting interventricular dyssynchrony are provided. In one embodiment, the apparatus includes an image segment processor and an image classifier. The image segment processor may segment left and right ventricles in source images of a subject's heart to form left and right ventricle segments in segmented images. Each source image may include cross sections of the right and left ventricles in common spatial relation along the short axis plane and in common temporal relation in reference to a cardiac cycle. The source images and corresponding segmented images may be temporally-spaced in relation to the cardiac cycle. The image classifier may determine first and second cross-sectional areas associated with the left and right ventricle segments for each segmented image, compare the first and second cross-sectional areas, and classify the subject's heart in an interventricular dyssynchronous class or a non-dyssynchronous class.

31 Claims, 12 Drawing Sheets

U.S. PATENT DOCUMENTS

| | | | |
|---|---|---|---|
| 5,785,654 A | 7/1998 | Iinuma et al. | |
| 5,797,396 A * | 8/1998 | Geiser et al. | 600/407 |
| 6,070,100 A | 5/2000 | Bakels et al. | |
| 6,231,518 B1 | 5/2001 | Grabek et al. | |
| 6,243,603 B1 | 6/2001 | Ideker et al. | |
| 6,327,499 B1 | 12/2001 | Alt | |
| 6,411,840 B1 | 6/2002 | Bardy | |
| 6,453,192 B1 | 9/2002 | Ding et al. | |
| 6,487,443 B2 | 11/2002 | Olson et al. | |
| 6,497,655 B1 | 12/2002 | Linberg et al. | |
| 6,636,764 B1 | 10/2003 | Fain et al. | |
| 6,662,032 B1 | 12/2003 | Gavish et al. | |
| 6,801,661 B1 | 10/2004 | Sotak et al. | |
| 6,810,282 B2 | 10/2004 | Taha et al. | |
| 6,816,266 B2 | 11/2004 | Varshneya et al. | |
| 6,871,088 B2 | 3/2005 | Chinchoy | |
| 6,885,889 B2 | 4/2005 | Chinchoy | |
| 6,978,184 B1 | 12/2005 | Marcus et al. | |
| 7,041,061 B2 | 5/2006 | Kramer et al. | |
| 7,043,063 B1 * | 5/2006 | Noble et al. | 382/128 |
| 7,421,101 B2 * | 9/2008 | Georgescu et al. | 382/128 |
| 7,613,500 B2 * | 11/2009 | Vass et al. | 600/427 |
| 2001/0024516 A1 * | 9/2001 | Yoshioka et al. | 382/128 |
| 2002/0016550 A1 | 2/2002 | Sweeney et al. | |
| 2002/0072934 A1 | 6/2002 | Ross et al. | |
| 2002/0087072 A1 * | 7/2002 | Breeuwer | 600/420 |
| 2002/0156389 A1 | 10/2002 | Kalgren et al. | |
| 2003/0031385 A1 | 2/2003 | Elad et al. | |
| 2003/0144700 A1 | 7/2003 | Brown et al. | |
| 2003/0153823 A1 | 8/2003 | Geiser et al. | |
| 2003/0204212 A1 | 10/2003 | Burnes et al. | |
| 2004/0006265 A1 | 1/2004 | Alhussiny | |
| 2004/0015081 A1 * | 1/2004 | Kramer et al. | 600/439 |
| 2004/0077934 A1 | 4/2004 | Massad | |
| 2004/0106960 A1 | 6/2004 | Siejko et al. | |
| 2004/0220625 A1 | 11/2004 | Silvestri et al. | |
| 2005/0004615 A1 | 1/2005 | Sanders | |
| 2005/0010120 A1 | 1/2005 | Jung et al. | |
| 2005/0075542 A1 | 4/2005 | Goldreich | |
| 2005/0096522 A1 * | 5/2005 | Reddy et al. | 600/407 |
| 2005/0100203 A1 * | 5/2005 | Fujisawa | 382/130 |
| 2005/0102002 A1 | 5/2005 | Salo et al. | |
| 2005/0107838 A1 | 5/2005 | Lovett et al. | |
| 2005/0115561 A1 | 6/2005 | Stahmann et al. | |
| 2005/0137634 A1 | 6/2005 | Hall et al. | |
| 2005/0142070 A1 | 6/2005 | Hartley et al. | |
| 2005/0149137 A1 | 7/2005 | Chinchoy et al. | |
| 2005/0256417 A1 | 11/2005 | Fischell et al. | |
| 2006/0020294 A1 | 1/2006 | Brockway et al. | |
| 2006/0095085 A1 | 5/2006 | Marcus et al. | |
| 2006/0116581 A1 | 6/2006 | Zdeblick et al. | |
| 2006/0262988 A1 | 11/2006 | Tek et al. | |
| 2007/0014452 A1 * | 1/2007 | Suresh et al. | 382/128 |
| 2007/0275083 A1 | 11/2007 | Xu et al. | |

FOREIGN PATENT DOCUMENTS

| | | |
|---|---|---|
| EP | 0653224 B1 | 1/2004 |
| EP | 1470836 A1 | 10/2004 |
| EP | 1470836 B1 | 1/2007 |
| WO | 01/36046 A1 | 5/2001 |
| WO | 01/70104 A2 | 9/2001 |
| WO | 03/003905 A2 | 1/2003 |
| WO | 03/047690 A2 | 6/2003 |
| WO | 2004/091720 A2 | 10/2004 |
| WO | 2004/103184 A2 | 12/2004 |
| WO | 2005/037355 A1 | 4/2005 |
| WO | 2005/046788 A2 | 5/2005 |
| WO | 2006/042039 A2 | 2/2006 |
| WO | 2006/050385 A2 | 5/2006 |
| WO | 2006/056221 A1 | 6/2006 |

OTHER PUBLICATIONS

Abraham et al., Cardiac resynchronization in chronic heart failure, N Engl J Med, 346: pp. 1845-1853 (2002).

Abraham et al., Cardiac resynchronization therapy for heart failure, Circulation, 108: pp. 2596-2603 (2003).

Adigun et al., Cardiac Resynchronization Therapy for Treatment of Congestive Heart Failure, Hospital Physician, pp. 15-17 and 24 (Jan. 2005).

Aletras et al., AIR-SPAMM: alternative inversion recovery spatial modulation of magnetization for myocardial tagging, J Magn Reson, 166: pp. 236-245 (2004).

Aletras et al., Mixed echo train acquisition displacement encoding with stimulated echoes: an optimized DENSE method for in vivo functional imaging of the human heart, Magnetic Resonance Medicine, 46: pp. 523-534 (2001).

Bax et al., Echocardiographic Evaluation of Cardiac Resynchronization Therapy: Ready for Routine Clinical Use?, Journal of the American College of Cardiology, vol. 44, No. 1, pp. 1-9 (Jul. 7, 2004).

Bellenger et al., Reduction in sample size for studies of remodeling in heart failure by the use of cardiovascular magnetic resonance, J Cardiovasc Magn Reson, 2: pp. 271-278 (2000).

Bristow et al., Cardiac-resynchronization therapy with or without an implantable defibrillator in advanced chronic heart failure, N Engl J Med, 350: pp. 2140-2150 (2004).

Chakraborty et al., Deformable boundary finding in medical images by integrating gradient and region information, IEEE Transactions on Medical Imaging, vol. 15, No. 6, pp. 859-870 (1996).

Cohen et al., Finite-element methods for active contour models and balloons for 2-D and 3-D images, IEEE Transactions on Pattern Analysis and Machine Intelligence, vol. 15, No. 11, pp. 1131-1147 (1993).

Cootes et al., Active appearance models, European Conference on Computer Vision, 2: pp. 484-498 (1998).

Cootes et al., Active shape models: Their training and application, Computer Vision and Image Understanding, 61: pp. 38-59 (1995).

Dekker et al., Epicardial left ventricular lead placement for cardiac resynchronization therapy: Optimal pace site selection with pressure-volume loops, The Journal of Thoracic and Cardiovascular Surgery, vol. 127, No. 6 pp. 1641-1647 (2004).

Dohi et al., Utility of Echocardiographic Tissue Synchronization Imaging to Redirect Left Ventricular Lead Placement for Improved Cardiac Resynchronization Therapy, PACE, vol. 28, pp. 461-465 (May 2005).

Duncan et al., Medical image analysis: Progress over two decades and the challenges ahead, IEEE Transactions on Pattern Analysis and Machine Intelligence, vol. 22, No. 1, pp. 85-106 (Jan. 2000).

Etesami et al., Automatic dimensional inspection of machine part cross-sections using Fourier analysis, Computer Vision, Graphics, and Image Processing, vol. 29, pp. 216-247 (1985).

Folkers et al., Content-based image retrieval using Fourier descriptors on a logo database, in Proc. ICPR, III: pp. 521-524 (2002).

Ghio et al., Interventricular and intraventricular dyssynchrony are common in heart failure patients, regardless of QRS duration, European Heart Journal, vol. 25, pp. 571-578 (2004).

Int'l App. No. PCT/US06/36384, International Search Report, 2 pages, mailed Sep. 13, 2007.

Int'l App. No. PCT/US06/36384, Written Opinion of the International Searching Authority, 3 pages, mailed Sep. 13, 2007.

Int'l App. No. PCT/US06/36385, International Search Report, 2 pages, mailed Apr. 2, 2007.

Int'l App. No. PCT/US06/36385, Written Opinion of the International Searching Authority, 4 pages, mailed Apr. 2, 2007.

Jain et al., Deformable template models: A review, Signal Processing, vol. d71, No. 2, pp. 109-129 (1998).

Jain et al., Statistical pattern recognition: A review, IEEE Trans. on PAMI, vol. 22, No. 1, pp. 4-37 (2000).

Kass et al., Snakes: Active contour models, International Journal on Computer Vision, vol. 1, No. 4, pp. 321-331 (Jan. 1988).

McInerney et al., Deformable models in medical image analysis, Medical Image Analysis, vol. 1, No. 2, pp. 91-108 (1996).

Mitchell et al., Multistage hybrid active appearance model matching: segmentation of left and right ventricles in cardiac MR images, IEEE Transactions on Medical Imaging, 20: pp. 415-423 (2001).

Molhoek et al., Effectiveness of resynchronization therapy in patients with end-stage heart failure, American Journal of Cardiology; 90: pp. 379-383 (2002).

Mule et al., Assessment of dyssynchrony in patients with severe heart failure by nuclear imaging: paradise lost and regained or lost and gone forever?, International Heart Journal, 6: pp. 96-105 (2005).

Procedures: Biventricular Pacemakers—What you need to know about biventricular pacing to treat heart failure, www.clevelandclinic.org/ heartcenter/ pub/ guide/ tests/ procedures/ biventricular_pm.htm, printed Jul. 3, 2006, Cleveland Clinic Foundation, Cleveland, OH, 10 pages (Jun. 2002).

Ranganath, Contour extraction from cardiac MRI studies using snakes, IEEE Transactions on Medical Imaging, vol. 14, No. 2, pp. 328-338 (1995).

Reichek, MRI myocardial tagging, Journal of Magnetic Resonance Imaging, 10: pp. 609-616 (1999).

Sarkar et al., Optimal infinite impulse response zero crossing based edge detectors, Computer Vision, Graphics and Image Processing, 54: pp. 224-243 (1991).

Schnurrenberger, Hierarchical classification and grouping of map spot symbols characterized by Fourier descriptors, M.S. thesis, Graduate School of the Ohio State University, Columbus, OH, 236 pages (1988).

Sogaard et al., Sequential Versus Simultaneous Biventricular Resynchronization for Severe Heart Failure—Evaluation by Tissue Doppler Imaging, Circulation, pp. 2078-2084 (Oct. 15, 2002).

Staib et al., Boundary finding with parametrically deformable models, IEEE Transactions on Pattern Analysis and Machine Intelligence, vol. 14, No. 11, pp. 1061-1075 (1992).

Stellbrink et al., The importance of being synchronous: On the prognostic value of ventricular conduction delay in heart failure, Journal of the American College of Cardiology, vol. 40, No. 11, pp. 2022, 2032, and 2033 (2002).

Suri et al., Shape recovery algorithms using level sets in 2-D/3-D medic: A state-of-the-art review, IEEE Transactions on Information Technology in Biomedicine, vol. 6, No. 1, pp. 8-28 (Mar. 2002).

Székely et al., Segmentation of 2-D and 3-D objects from MRI volume data using constrained elastic deformations of flexible Fourier contour and surface models, Medical Image Analysis, vol. 1, No. 1, pp. 19-34 (1996).

Xu et al., Snakes, shapes, and gradient vector' flow, IEEE Transactions on Image Processing, vol. 7, No. 3, pp. 359-369 (Mar. 1998).

Yu et al., A novel tool to assess systolic asynchrony and identify responders of cardiac resynchronization therapy by tissue synchronization imaging, J Am Coll Cardiol, 45: pp. 677-684 (2005).

Yu et al., Understanding Nonresponders of Cardiac Resynchronization Therapy—Current and Future Perspectives, Journal of Cardiovascular Electrophysiology, vol. 16, No. 10, pp. 1117-1124 (Oct. 2005).

Zhong et al., Object tracking using deformable templates, IEEE Transactions on Pattern Analysis and Machine Intelligence, vol. 22, No. 5, pp. 544-549 (May 2000).

Zhu et al., Selecting Principal Components in a Two-Stage LDA Algorithm, Proceedings of the IEEE Conference on Computer Vision and Pattern Recognition, vol. 1, pp. 132-137 (2006).

Seul et al., p. 145 from Practical Algorithms for Image Analysis, copyright 2000.

Seber et al., pp. 4-5 and 97-99 from Linear Regression Analysis, copyright 2003.

Office Action issued Jul. 22, 2011 in related U.S. Appl. No. 12/067,093.

Huang et al., A content-based image retrieval system, Image and Computing, vol. 16, 1998, pp. 149-163.

Jouan, Analysis of Sequence of Cardiac Contours by Fourier Descriptors for Plane Closed Curves, IEEE Transactions on Medical Imaging, vol. M1-6. No. 2. Jun. 1987. pp. 176-180.

Office Action issued Dec. 23, 2011 in related U.S. Appl. No. 12/067,093.

\* cited by examiner

METHOD AND APPARATUS FOR DETECTING INTERVENTRICULAR DYSSYNCHRONY

CROSS-REFERENCE TO RELATED APPLICATIONS

This application claims the benefit of U.S. provisional patent application, Ser. No. 60/718,115, filed Sep. 16, 2005. This application is also related to co-pending PCT patent application entitled "Method and Apparatus for Detecting Intraventricular Dyssynchrony" by Paulo F. U. Gotardo, Kim L. Boyer and Subha V. Raman (PCT/US06/36385) filed with the U.S. Patent and Trademark Office (USPTO) the same day as this application. The contents of all above-identified patent application(s) and patent(s) are fully incorporated herein by reference.

BACKGROUND

Interventricular dysynchrony is a condition where the right and left ventricles fail to contract in phase. In a normal heart, both ventricles beat together and are effectively "synchronized." When the ventricles are dyssynchronous, there is a lack of coordinated mechanical activity of the ventricles. This contributes to the evolution of ventricular dysfunction and symptomatic congestive heart failure. Biventricular pacing, a form of cardiac resynchronization therapy (CRT), is an approved modality for treating ventricular failure when interventricular dysynchrony is present and has been shown to improve survival as well as symptoms in patients with congestive heart failure. Response to CRT, however, is variable and, in the past, has been difficult to predict. For example, studies have shown that over 30 percent of patients receiving CRT may not respond to the treatment.

Based on the foregoing, accurate detection of interventricular dysynchrony is not well established. This may be in part due to insufficient characterization of interventricular dyssynchrony by current diagnostic techniques. For example, quantitative detection methods have been based oil data from electrocardiography (EKG) or tissue Doppler echocardiography (echo) tests. For example, selection of patients for CRT has been based on EKG measurements of QRS duration ($\geq 130$ ms) and ejection fraction ($\leq 35\%$). However, EKG data is only a gross estimate of disordered electical and mechanical activation of the ventricles. As for the echo test, it is difficult to administer (especially for the right ventricle) because the operator must locate an acoustic window within which the selected ventricle can be detected by the echo probe. Also, the echo test only captures displacement and velocity information for a small target area on the inner wall of the selected ventricle. Processing the echo data is time intensive. Nevertheless, the results from echo tests suggest that EKG tests are too insensitive and inconclusive. In other words, some patients that appear to exhibit interventricular dyssynchrony in the echo test are not diagnosed as such from EKG results.

Medical imaging techologies (e.g., cardiac magnetic resonance imaging (MRI)) capable of capturing the cardiac cycle have been used to qualitatively diagnose interventricular dysynchrony through observation of motion sequences showing operation of the ventricles over the cardiac cycle. However, this is a subjective test and requires the experience and expertise of a cardiologist. Nevertheless, this qualitative technique also suggests that EKG tests are too insensitive and inconclusive.

Information related to attempts to address these problems can be found, for example, in PCT Patent Application Publication Number WO 2006/042039 and U.S. Pat. Nos. 6,978,184 and 7,041,061. However, each one of these references requires insertion of a medical instrument (e.g., catheter) or implantation of a medical device (e.g., pacemaker, CRT device, etc.) in the patient in order to test for dyssynchrony. Based at least on the foregoing, there is a need for an improved method and apparatus for detecting interventricular dyssynchrony.

SUMMARY

In one aspect, an apparatus for detecting interventricular dyssynchrony is provided. In one embodiment, the apparatus includes: an image segment processor segmenting a left ventricle and a right ventricle in each of a plurality of source images of a heart to form left and right ventricle segments in a corresponding plurality of segmented images, each source image including at least a portion of a cross section of the heart along a short axis plane, each source image including cross sections of the right and left ventricles of the heart in common spatial relation along the short axis plane and in common temporal relation in reference to a cardiac cycle associated with the heart, the plurality of source images and corresponding plurality of segmented images being temporally-spaced in relation to the cardiac cycle and an image classifier, in operative communication with the image segment processor, determining a first cross-sectional area associated with the left ventricle segment and a second cross-sectional area associated with the right ventricle segment for each segmented image, comparing the first and second cross-sectional areas for each segmented image, and classifying the heart in an interventricular dyssynchronous class or a non-dyssynchronous class based at least in part on the comparing.

In another embodiment, the apparatus includes: an image segment processor segmenting a left ventricle and a right ventricle from one or more source images of a heart to form left and right ventricle segments in one or more segmented images, each source image including at least a portion of a cross section of the heart along a short axis plane, the one or more source images, at least in combination, including cross sections of right and left ventricles of the heart in common spatial relation along the short axis plane and in common temporal relation to a cardiac cycle associated with the heart and an image classifier, in operative communication with the image segment processor, determining a first cross-sectional area associated with the left ventricle segment and a second cross-sectional area associated with the right ventricle segment, comparing the first and second cross-sectional areas, and classifying the heart in an interventricular dyssynchronous class or a non-dyssynchronous class based at least in part on the comparing.

In another aspect, a method of detecting interventricular dyssynchrony is provided. In one embodiment, the method includes: a) receiving a plurality of source images of a heart, each source image including at least a portion of a cross section of the heart along a short axis plane, each source image including cross sections of right and left ventricles of the heart in common spatial relation along the short axis plane and in common temporal relation in reference to a cardiac cycle associated with the heart, the plurality of source images being temporally-spaced in relation to the cardiac cycle, b) segmenting the left ventricle and the right ventricle in each source image to form left and right ventricle segments in a corresponding plurality of segmented images, c) determining a first cross-sectional area associated with the left ventricle segment and a second cross-sectional area associated with the right ventricle segment for each segmented image, d) comparing the first and second cross-sectional areas for each segmented image, and e) classifying the heart in an interventricular dyssynchronous class or a non-dyssynchronous class based at least in part on the comparing.

In another embodiment, the method includes: a) receiving one or more source images of a heart, each source image including at least a portion of a cross section of the heart along a short axis plane, the one or more source images, at least in combination, including cross sections of right and left ventricles of the heart in common spatial relation along the short axis plane and in common temporal relation to a cardiac cycle associated with the heart, b) segmenting the left ventricle and the right ventricle from the one or more source images to form left and right ventricle segments in one or more segmented images, c) determining a first cross-sectional area associated with the left ventricle segment and a second cross-sectional area associated with the right ventricle segment from the one or more segmented images, d) comparing the first and second cross-sectional areas, and e) classifying the heart in an interventricular dyssynchronous class or a non-dyssynchronous class based at least in part on the comparing.

DRAWINGS

These and other features, aspects, and advantages of the present invention will become better understood with regard to the accompanying drawings, following description, and appended claims.

DESCRIPTION

Figure 1:
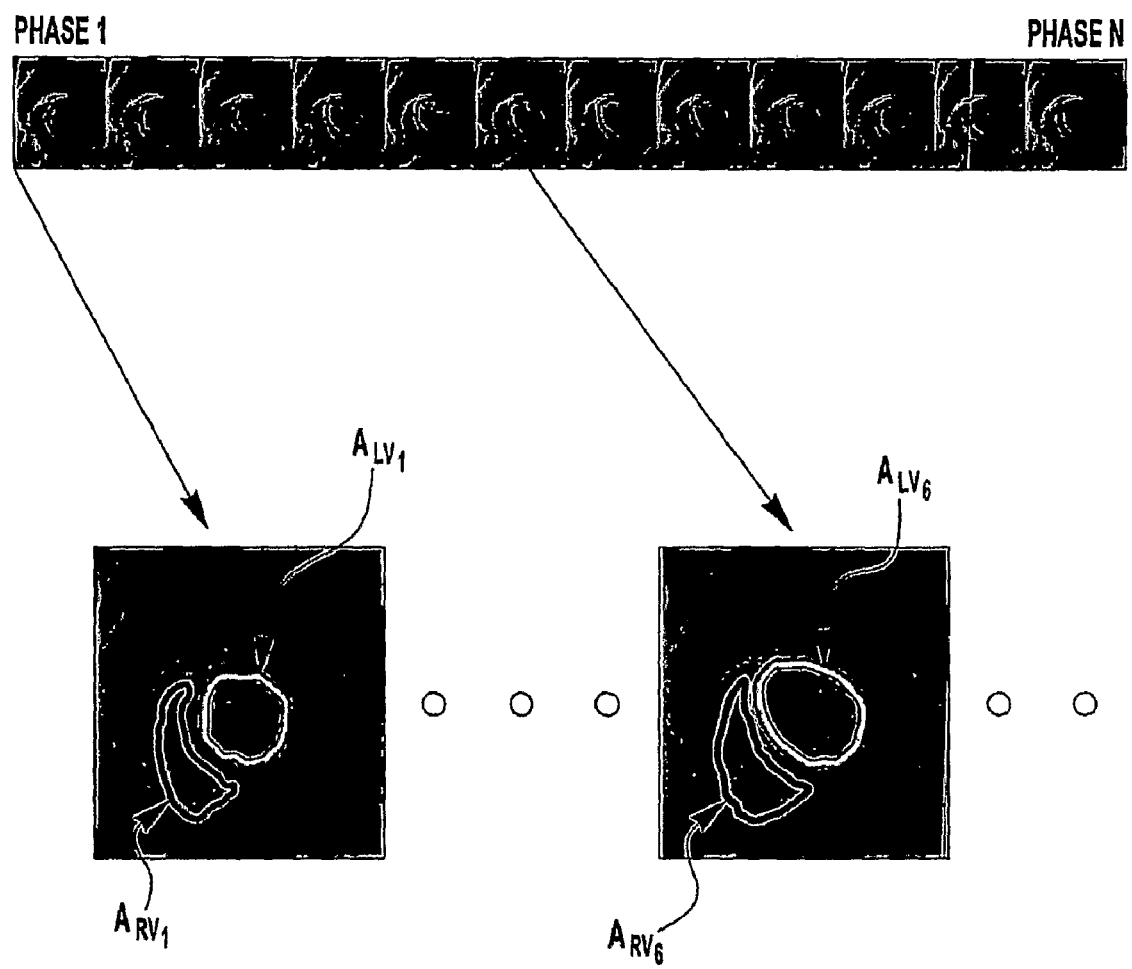
FIG. 1 shows an exemplary sequence of images showing a mid-cavity cross-sectional view of left and right ventricles in relation to an exemplary subject's cardiac cycle along a short axis of the exemplary subject's heart as well as segmentation of the left and right ventricles.

The following paragraphs include definitions of exemplary terms used within this disclosure. Except where noted otherwise, variants of all terms, including singular forms, plural forms, and other affixed forms, fall within each exemplary term meaning. Except where noted otherwise, capitalized and non-capitalized forms of all terms fall within each meaning.

"Circuit," as used herein includes, but is not limited to, hardware, firmware, software or combinations of each to perform a function(s) or an action(s). For example, based on a desired feature or need, a circuit may include a software controlled microprocessor, discrete logic such as an application specific integrated circuit (ASIC), or other programmed logic device. A circuit may also be fully embodied as software. As used herein, "circuit" is considered synonymous with "logic."

"Comprising," "containing," "having," and "including," as used herein, except where noted otherwise, are synonymous and open-ended. In other words, usage of any of these terms (or variants thereof) does not exclude one or more additional elements or method steps from being added in combination with one or more enumerated elements or method steps.

"Computer component," as used herein includes, but is not limited to, a computer-related entity, either hardware, firmware, software, a combination thereof, or software in execution. For example, a computer component can be, but is not limited to being, a process running on a processor, a processor, an object, an executable, a thread of execution, a program and a computer. By way of illustration, both an application running on a server and the server can be computer components. One or more computer components can reside within a process or thread of execution and a computer component can be localized on one computer or distributed between two or more computers.

"Computer communication," as used herein includes, but is not limited to, a communication between two or more computer components and can be, for example, a network transfer, a file transfer, an applet transfer, an email, a hypertext transfer protocol (HTTP) message, a datagram, an object transfer, a binary large object (BLOB) transfer, and so on. A computer communication can occur across, for example, a wireless system (e.g., IEEE 802.11), an Ethernet system (e.g., IEEE 802.3), a token ring system (e.g., IEEE 802.5), a local area network (LAN), a wide area network (WAN), a point-to-point system, a circuit switching system, a packet switching system, and so on.

"Controller," as used herein includes, but is not limited to, any circuit or device that coordinates and controls the operation of one or more input or output devices. For example, a controller can include a device having one or more processors, microprocessors, or central processing units (CPUs) capable of being programmed to perform input or output functions "Logic," as used herein includes, but is not limited to, hardware, firmware, software or combinations of each to perform a function(s) or an action(s), or to cause a function or action from another component. For example, based on a desired application or need, logic may include a software controlled microprocessor, discrete logic such as an application specific integrated circuit (ASIC), or other programmed logic device. Logic may also be fully embodied as software. As used herein, "logic" is considered synonymous with "circuit."

"Measurement," as used herein includes, but is not limited to, an extent, magnitude, size, capacity, amount, dimension, characteristic or quantity ascertained by measuring. Example measurements are provided, but such examples are not intended to limit the scope of measurements the systems and methods described herein can employ.

"Operative communication," as used herein includes, but is not limited to, a communicative relationship between devices, logic, or circuits, including mechanical and pneumatic relationships. Direct electrical, electromagnetic, and optical connections and indirect electrical, electromagnetic, and optical connections are examples of such communications. Linkages, gears, chains, push rods, cams, keys, attaching hardware, and other components facilitating mechanical connections are also examples of such communications. Pneumatic devices and interconnecting pneumatic tubing may also contribute to operative communications. Two devices are in operative communication if an action from one causes an effect in the other, regardless of whether the action is modified by some other device. For example, two devices separated by one or more of the following: i) amplifiers, ii) filters, iii) transformers, iv) optical isolators, v) digital or analog buffers, vi) analog integrators, vii) other electronic circuitry, viii) fiber optic transceivers, ix) Bluetooth communications links, x) 802.11 communications links, xi) satellite communication links, and xii) other wireless communication links. As another example, an electromagnetic sensor is in operative communication with a signal if it receives electromagnetic radiation from the signal. As a final example, two devices not directly connected to each other, but both capable of interfacing with a third device, e.g., a central processing unit (CPU), are in operative communication.

"Or," as used herein, except where noted otherwise, is inclusive, rather than exclusive. In other words, "or' is used to describe a list of alternative things in which one may choose one option or any combination of alternative options. For example, "A or B" means "A or B or both" and "A, B, or C" means "A, B, or C, in any combination." If "or" is used to indicate an exclusive choice of alternatives or if there is any limitation on combinations of alternatives, the list of alternatives specifically indicates that choices are exclusive or that certain combinations are not included. For example, "A or B, but not both" is used to indicate use of an exclusive "or" condition. Similarly, "A, B, or C, but no combinations" and "A, B, or C, but not the combination of A, B, and C" are examples where certain combination of alternatives are not included in the choices associated with the list.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software," as used herein includes, but is not limited to, one or more computer readable or executable instructions that cause a computer or other electronic device to perform functions, actions, or behave in a desired mainer. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system, or other types of executable instructions. It will be appreciated by one of ordinary skill in the art that the form of software is dependent on, for example, requirements of a desired application, the environment it runs on, or the desires of a designer/programmer or the like.

"Software component," as used herein includes, but is not limited to, a collection of one or more computer readable or executable instructions that cause a computer or other electronic device to perform functions, actions or behave in a desired manner. The instructions may be embodied in various forms like routines, algorithms, modules, methods, threads, or programs. Software components may be implemented in a variety of executable or loadable forms including, but not limited to, a stand-alone program, a servlet, an applet, instructions stored in a memory, and the like. Software components can be embodied in a single computer component or can be distributed between computer components.

The following table includes long form definitions of exemplary acronyms used within this disclosure. Except where noted otherwise, variants of all acronyms, including singular forms, plural forms, and other affixed forms, fall within each exemplary acronym meaning. Except where noted otherwise, capitalized and non-capitalized forms of all acronyms fall within each meaning.

| Acronym | Long Form |
|---|---|
| 2D | Two-Dimensional |
| 3D | Three-Dimensional |
| AAM | Active Appearance Model |
| ASIC | Application Specific Integrated Circuit |
| ASM | Active Shape Model |
| BLOB | Binary Large Object |
| CBE | Cardiovascular Bioengineering Enterprise |
| CMR | Cardiac Magnetic Resonance |
| CPU | Central Processing Unit |
| CRT | Cardiac Resynchronization Therapy |
| CT | Computed Tomography |
| DICOM | Digital Imaging And Communications In Medicine |
| DSP | Digital Signal Processor |
| echo | Echocardiography or Echocardiogram |
| EKG | Electrocardiography or Electrocardiograph |
| EPROM | Erasable Programmable Read-Only Memory |
| FDA | Food and Drug Administration |
| FFE | Fast Field Echo |
| FISP | Fast Imaging With Steady Precession |
| GE | General Electric |
| GVF | Gradient Vector Flow |
| HTTP | Hypertext Transfer Protocol |
| IEEE | Institute of Electrical and Electronics Engineers |
| ISDN | Integrated Services Digital Network |
| LAN | Local Area Network |
| LDA | Linear Discriminant Analysis |
| LED | Light Emitting Diode |
| LV | Left Ventricle |
| MAP | Maximum A-Posteriori |

| Acronym | Long Form |
|---|---|
| MDA | Mixture Discriminant Analysis |
| MDCT | Multi-Detector Computer Tomography |
| MLE | Maximum Likelihood Estimate |
| MR | Magnetic Resonance |
| MRI | Magnetic Resonance Imaging |
| ms | Millisecond |
| NYHA | New York Heart Association |
| OZCO | Optimal Zero Crossing Operator |
| PC | Personal Computer |
| PCA | Principal Component Analysis |
| PET | Positron Emission Tomography |
| POTS | Plain Old Telephone System |
| PROM | Programmable Read-Only Memory |
| QRS | Q, R, and S points in an electrical signal representing a cardiac cycle |
| RAM | Random Access Memory |
| RF | Radio Frequency |
| ROM | Read-Only Memory |
| RV | Right Ventricle |
| SPECT | Single Photon Emission Computer Tomography |
| SSFP | Steady-State Free Precession |
| true-FISP | True Fast Imaging With Steady Precession |
| V-V | Ventricle-to-Ventricle |
| WAN | Wide Area Network |
| ZC | Zero Crossing |

In an exemplary embodiment, a method of detecting interventricular dyssynchrony may include imaging the left and right ventricles in relation to a subject's cardiac cycle along a short axis of the subject's heart using a suitable medical imaging device and exploring the degree of interventricular synchronous activity by processing and analyzing the cross-sectional areas of the ventricles from the image information. The specific view of the images along the short axis, for example, may be a mid-cavity view. These results may provide a more sensitive definition of interventricular dyssynchrony than previous methods. This may allow more accurate identification of patients who will benefit from CRT than previous methods. Accordingly, the method may provide quantitative diagnostic criteria for detection of interventricular dyssynchrony that is more accurate than previous diagnostic methods.

For example, in one embodiment, the image data may be acquired using standard cine techniques for a sequence of temporally-spaced mid-cavity short axis images of the ventricles in a suitable cardiac MRI device, such as a model Signa HDe 1.5T™ MRI device from GE Healthcare with headquarters in London, United Kingdom. This exemplary unit is a 1.5 Tesla device. In other embodiments, other views along the short axis may be used. In the embodiment being described, the identification, processing, and analyzing of the cross-sectional areas of the ventricles may be characterized as an add-on to standard cardiac MRI technology. In this regard, the identification, processing, and analyzing of the cross-sectional areas of the ventricles may be co-located within the cardiac MRI device or within an independent computer that is in operative communication with the cardiac MRI device. In either configuration, the corresponding diagnostic test results for interventricular dyssynchrony could be selected as an optional output of a standard cardiac MRI study.

In other embodiments, the image data may be acquired using any type of medical imaging modality capable of capturing or constructing a temporally-spaced two-dimensional (2D) sequence of cross-sectional short axis images of the ventricles of a subject's heart. For example, radiography, tomography, medical sonography, or nuclear medicine technologies may be used in any combination capable of providing such a 2D sequence. More specifically, the image data may be acquired using echo, multi-detector computed tomography (MDCT), single photon emission computed tomography (SPECT), or positron emission tomography (PET) modalities as well as cardiac MRI or other suitable modalities.

Generally, biventricular pacing (i.e., a form of CRT) is a therapy for symptomatic congestive heart failure that has been approved by the Food and Drug Administration (FDA). CRT has been proven effective for improving survival as well as symptoms in patients who are diagnosed with dyssynchronous ventricular mechanical activity (e.g., interventricular dyssynchrony). Theoretically, interventricular dyssynchrony means failure of the right and left ventricles to contract in a coordinated fashion. This may lead to evolution or progression of symptomatic heart failure. However, previous techniques for diagnosing interventricular dyssynchrony have not established reliable quantitative criterion upon which it can be defined. Therefore, clinically, the definition of interventricular dyssynchrony has relied, for example, on EKG criteria which identifies certain measurements for QRS duration ($\geq$130 ms) and ejection fraction ($\leq$35%). However, these are only a gross estimate of disordered electrical and mechanical ventricular activation. Accordingly, many patients who may benefit from CRT are not diagnosed under the EKG criteria. The diagnostic technique for interventricular dyssynchrony described herein may provide a readily applicable, sensitive standard for the identification of interventricular dyssynchrony that can be broadly applied to patients with congestive heart failure.

In one embodiment, a method for detecting interventricular dyssynchrony may include acquiring image data via a cardiac MRI scan of a subject's heart, constructing a cine sequence in temporal relation to a cardiac cycle for the subject that shows cross-sections of the right and left ventricles from a mid-cavity view along a short axis of the subject's heart, segmenting the right and left ventricles within the cine sequence in relation to outer walls of the corresponding ventricles, determining cross-sectional areas for the right and left ventricles in each image of the cine sequence, and analyzing the cross-sectional areas of the left and right ventricles using a linear regression model. In other embodiments, the image data may be acquired using any type of medical imaging modality capable of capturing or constructing a 2D sequence of cross-sectional short axis images of the ventricle of a subject's heart. In another embodiment, the images of the cine sequence may be from an alternate view along the short axis of the subject's heart.

The cross-sectional area of the left ventricle may be specified, for example, as a dependent variable and the cross-sectional area of the right ventricle may be specified, for example, as an independent variable in the linear regression model. In another embodiment, the dependent and independent variables could be swapped. If the right and left ventricles contract in a synchronous fashion, a linear relation between the cross-sectional areas of the right and left ventricles throughout the cardiac cycle is expected due to the similar time sequence of electrical activation and ventricular contraction. Dyssynchronous activity will not exhibit such a linear relation. Synchrony by this technique may be defined as a statistically significant ($p<0.05$) least squares regression of the cross-sectional area of the left ventricle in relation to the cross-sectional area of the right ventricle. Regressions that fail to attain statistical significance may also be defined as dyssynchronous.

A sequence of images (e.g., cine) in a short axis plane (and relating to a cardiac cycle) of a subject's heart may be used as input to another embodiment of the method for detecting interventricular dyssynchrony. These images may be obtained using a standard clinical MRI system configured for cardiac imaging and equipped with standard pulse sequences (e.g., steady-state free precession (SSFP), true fast imaging with steady state precession (true-FISP) techniques). The input images can be acquired using subject breath hold, cardiac gating (e.g., EKG), continuous real-time, or any combination of these acquisition procedures. The resulting sequence of images is expected to relate to the subject's overall cardiac cycle. A segmented data acquisition process may be used to acquire images or partial images (e.g., 8-16 lines) over a series of cardiac cycles. With the segmented data process, the cine is a sequence of constructed images advancing through an exemplary synthesized cardiac cycle for the subject because each image is actually acquired during multiple cardiac cycles. The synthesized cardiac cycle is representative of a typical cardiac cycle for the subject.

The cine sequence may be transferred from the imaging device to a workstation or PC equipped with software for measuring the cross-sectional areas of the right and left ventricles. The cine sequence may be transferred in a file format compatible with the Digital Imaging and Communications in Medicine (DICOM) standard. An image processing software application may be used to segment and measure the cross-sectional areas of the ventricles, such as NIHimage freeware, a public domain Java program by Wayne Rasband of Kensington, Md. Delineation of the endocardial contours of the right and left ventricles within each cine image may be done either manually or semi-automatically to segment the right and left ventricles. For example, the image processing software application may be used to identify edges within a given image. The edges corresponding to the outer walls of the right and left ventricles may be selected to segment the desired cross-sectional areas within a given image. The area surrounded by the selected edges may be determined, for example, by the image processing software application using any suitable mathematical technique. Upon completion of the segmentation and cross-sectional area computations, there will be a cross-sectional area for the right and left ventricles for each image of the cine sequence. The ultimate cine sequence has a temporal relationship to the subject's cardiac cycle. The resulting cross-sectional areas for the right and left ventricle over time may be provided as independent and dependent variables, respectively, for linear regression modeling.

The method and apparatus for detecting interventricular dyssynchrony described herein was implemented in 17 patients who underwent cardiac MRI as part of a prospective study of patients with cardiovascular disease funded by the Cardiovascular Bioengineering Enterprise (CBE). Cine cardiac MRI images were obtained on one of two 1.5 Tesla MRI devices using both SSFP and true-FISP pulse sequences for image acquisition.

Statistical analysis comparing this approach to diagnosis of dyssynchrony based on EKG data showed that this method identified patients with interventricular dyssynchrony that exhibited normal QRS duration, as well as patients without interventricular dyssynchrony that exhibited abnormal QRS duration. This indicates that the method and apparatus for detecting interventricular dyssynchrony described herein is more sensitive than the method based on EKG data. Moreover, this shows that the method based on EKG data may be both over-inclusive and under-inclusive for detection of dyssynchrony.

In one embodiment of a method and apparatus for detecting interventricular dyssynchrony, the right and left ventricular cross-sectional areas can be determined by algorithms tracking operator-selected regions of interest. Linear regression analysis can be applied to the values determined for the cross-sectional areas by a software application program providing standard linear regression analysis. For example, this technique can be implemented as an additional form of post image processing with respect to standard image processing in a cardiac MRI device. This post image processing application can be used as an automated diagnostic standard that processes standard cardiac MRI images to identify patients with interventricular dyssynchrony who may benefit from CRT.

As discussed above, the technique for detection of interventricular dyssynchrony described herein uses short axis cardiac images generated by any standard cardiac imaging technique. For example, cine cardiac magnetic resonance (CMR) images may be used (see FIG. 1). CMR images are generally known to have superior spatial resolution and image quality compared to other cardiac imaging modalities. However, any type of medical imaging modality capable of capturing or constructing a temporally-spaced 2D sequence of cross-sectional short axis images of the ventricles of a subject's heart may be used.

Figure 2:
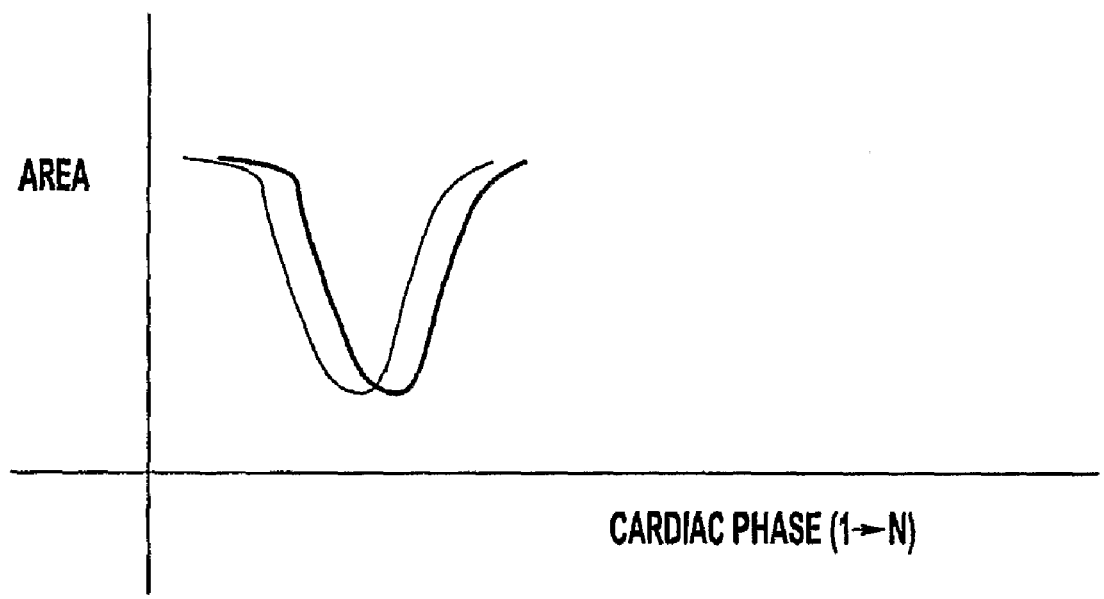
FIG. 2 shows a plot of exemplary cross-sectional areas of the right ventricle and left ventricle over time in relation to an exemplary subject's cardiac cycle.

From the cine CMR image set (i.e., phase 1 through phase N), as shown in FIG. 1, the right and left ventricles are segmented by identifying the endocardial borders of the right and left ventricles in each phase (i.e., each image). The resulting cross-sectional areas defined by the endocardial border contours for each phase of the cine CMR image set can be plotted (see FIG. 2). A correlation between these two cross-sectional areas ($A_{RV}$ and $A_{LV}$) may provide an output that can be analyzed for discrimination between hearts with interventricular dyssynchrony and hearts without interventricular dyssynchrony. For example, a linear regression analysis using the cross-sectional areas of the right and left ventricles as independent and dependent variables may be used to discriminate between results that are more linear (i.e., non-dyssynchronous or synchronous) and those that are less linear (i.e., interventricular dyssynchrony). In other words, a patient with interventricular dyssynchrony may have a poorer linear regression between the cross-sectional area-phase curves than a patient with synchronous contraction of the right and left ventricles.

In other embodiments, a cine or temporally-spaced 2D sequence of cross-sectional short axis images of the ventricles of a subject's heart in relation to a cardiac cycle for the subject may be provided from other types of medical imaging modalities, such as echo, nuclear medicine (e.g., SPECT, PET, etc.), computed tomography (CT), for example, using a spiral sequence (e.g., MDCT, etc.), in addition to cardiac MRI.

In further embodiments of the method and apparatus for detecting interventricular dyssynchrony, additional analysis of the characteristics of the cross-sectional areas of the right and left ventricles in patients from an interventricular dyssynchronous class may provide statistical patterns associated with interventricular dyssynchronous subclasses. In particular, such statistical patterns and subclasses may correlate to adjustable parameters associated with CRT. For example, in sequential biventricular pacing, a form of CRT, an optimum interventricular delay may be selected based on a patient showing interventricular dyssynchrony in a certain subclass.

As discussed above, the method and apparatus for detecting interventricular dyssynchrony described herein provides an image-guided selection of patients who would benefit from CRT. This selection is based on quantitative diagnostic test results that are able to associate patients with an interventricular dyssynchronous class or a non-dyssynchronous class.

The quantitative results from the diagnostic tests may translate into optimized CRT either through a mathematical relation or sub-class correlation. The mathematical relation may include a proportional relation or a more complex relation. For example, in sequential biventricular pacing, an optimum interventricular delay may be selected based on applying a predetermined mathematical function to certain quantitative results from the diagnostic tests.

Additionally, certain quantitative results from the diagnostic test may provide patterns indicative of interventricular dyssynchronous subclasses that relate to certain values for adjustable parameters associated with CRT. For example, the optimum interventricular delay for sequential biventricular pacing may be determined from the interventricular dyssynchronous subclasses indicated by the quantitative results of the diagnostic test. In other words, the output of the classifier described herein may be used to program ventricle-to-ventricle (V-V) delay (i.e., the delay between right and left ventricular activation) in CRT devices.

In one embodiment, a measure of interventricular dyssynchrony may be generated by comparing certain characteristics of right and left ventricular cross sectional areas. The right ventricular cross sectional areas measured throughout one complete cardiac cycle (i.e., the period extending from the start of ventricular contraction or systole to the completion of ventricular relaxation, or end-diastole) may be entered into one column of a data worksheet. Similarly, the left ventricular cross sectional areas measured throughout one complete cardiac cycle and corresponding to those measured for the right ventricle may be entered into the second column of the data worksheet.

Standard least squares regression analysis may be performed to relate corresponding right and left ventricular areas throughout the cardiac cycle. The right ventricular area may be designated to be the independent variable and the left ventricular area may be designated as the dependent variable. However, the same results would be obtained if instead the right ventricular area were designated as the dependent variable and the left ventricular area were designated as the independent variable. For example, the linear least squares regression model may be defined as:

$$\text{Left Ventricular Area} = B_o + B_1 * (\text{Right Ventricular Area}) + E \quad \quad 1),$$

where $B_o$ is an intercept and $B_1$ is the slope of the linear regression relating right and left ventricular areas. E is the error term describing the difference between the left ventricular areas predicted by the linear regression and the actual measures of the left ventricular areas. The worksheet containing the left and right ventricular areas may be imported into a wide variety of readily available statistical software packages to perform a standard least squares regression which may be used to estimate $B_o$ and $B_1$. Using this standard technique, $B_o$ and $B_1$ may be estimated such that the square of the error ($E^2$) between the predicted values for the left ventricular area and the actual measures of the left ventricular area is minimized.

The results of the least squares regression may be used to designate the presence or absence of interventricular synchrony. Interventricular synchrony may be present when the linear regression model described above is determined to be statistically significant. If the right and left ventricular areas throughout the cardiac cycle are described by a statistically significant linear relationship, it may be concluded that the right and left ventricular areas are generally equivalent throughout the cardiac cycle and that the two ventricles are contracting at a similar rate over time and are thus synchronous. Conversely, if the relationship between right and left ventricular areas over the cardiac cycle are not described by a statistically significant linear relationship, it may be concluded that the two ventricles are generally not contracting at equivalent rates over time and are thus dyssynchronous.

A statistically significant linear relationship may be defined by standard statistical techniques using the F test. This test is computed as the Regression Sums of Squares (i.e., the sum of the squared differences of the predicted value for the left ventricular area for each time point and the overall mean of left ventricular areas) divided by the Mean Square Error (i.e., the sum of the squared differences between the measured left ventricular areas and the left ventricular areas predicted by the regression relation divided by its degrees of freedom). This relationship may follow an F distribution and, if significantly large, may indicate that the linear regression model explains the variation of left ventricular area by the change in right ventricular area to a degree that is better than a model that does not include the right ventricular areas.

An equivalent test of whether the data are fit by a linear model may be to examine the statistical significance of $B_1$ the coefficient of the regression relating left and right ventricular areas. This may be performed using a T test consisting of the value of the coefficient divided by its standard error. A significant value indicates that the coefficient is different than 0 and thus a linear relationship exists.

Other tests of the linear relationship can be used to assess interventricular synchrony. These include, but are not limited to, the Coefficient of Determination (i.e., $R^2$) which is defined as the ratio of the Sum of Squared Errors to the Total Sums of Squares. The Coefficient of Determination indicates the percentage of variation in left ventricular area that is explained by variation in right ventricular area. Values greater than 0.5 may be considered as showing significant variation between the areas and are indicative of synchrony. The square root of $R^2$ (i.e., r) is the correlation coefficient and may similarly be used to measure the relationship between changes in left and right ventricular areas. Correlation coefficient values greater than 0.7, which correspond to greater than 50% variation in left ventricular area explained by the changes in right ventricular area, indicate the presence of synchrony.

Table 1 below contains right ventricular (RV) areas measured throughout the cardiac cycle in the first column and corresponding left ventricular (LV) areas measured throughout the cardiac cycle in the second column.

TABLE 1

| RV | LV |
|---|---|
| 2908 | 4291 |
| 2951 | 4179 |
| 2914 | 4012 |
| 2940 | 3986 |
| 2758 | 3689 |
| 2460 | 3487 |
| 2419 | 3549 |
| 2465 | 3617 |
| 2674 | 3622 |
| 2784 | 3554 |
| 2886 | 3682 |
| 2986 | 3745 |
| 2884 | 3908 |
| 2925 | 3991 |
| 2995 | 4008 |
| 2972 | 3932 |
| 3081 | 3949 |
| 3172 | 3986 |
| 3159 | 4109 |
| 3245 | 4166 |

As shown in the following example, data tabulated in the fashion shown in the above table may be submitted to a commercial statistical software package, such as STATA from StataCorp LP of College Station, Tex., to test for the presence of a significant linear relationship between RV and LV areas. Table 2 below is an example of an analysis printout from STATA for a patient classified as having synchronous ventricular function.

TABLE 2

| regress rv lvwaits | | | | | Number of obs = | 20 |
|---|---|---|---|---|---|---|
| | | | | | $F(1, 18) =$ | 93.78 |
| Source | ss | df | MS | | Prob > F = | 0.0000 |
| Model | 772541.305 | 1 | 772541.305 | | R-squared = | 0.8390 |
| Residual | 148277.645 | 18 | 8237.64692 | | Adj R-squared = | 0.8300 |
| Total | 920818.95 | 19 | 48464.1553 | | Root MSE = | 90.761 |
| rv | Coef. | Std. Err. | t | P > |t| | [95% Conf. Interval] | |
| lvwaits | 1.879861 | .1941183 | 9.68 | 0.000 | 1.472033 | 2.287688 |
| _cons | −3552.745 | 474.9947 | −7.48 | 0.000 | −4550.672 | −2554.818 |

Figure 3:
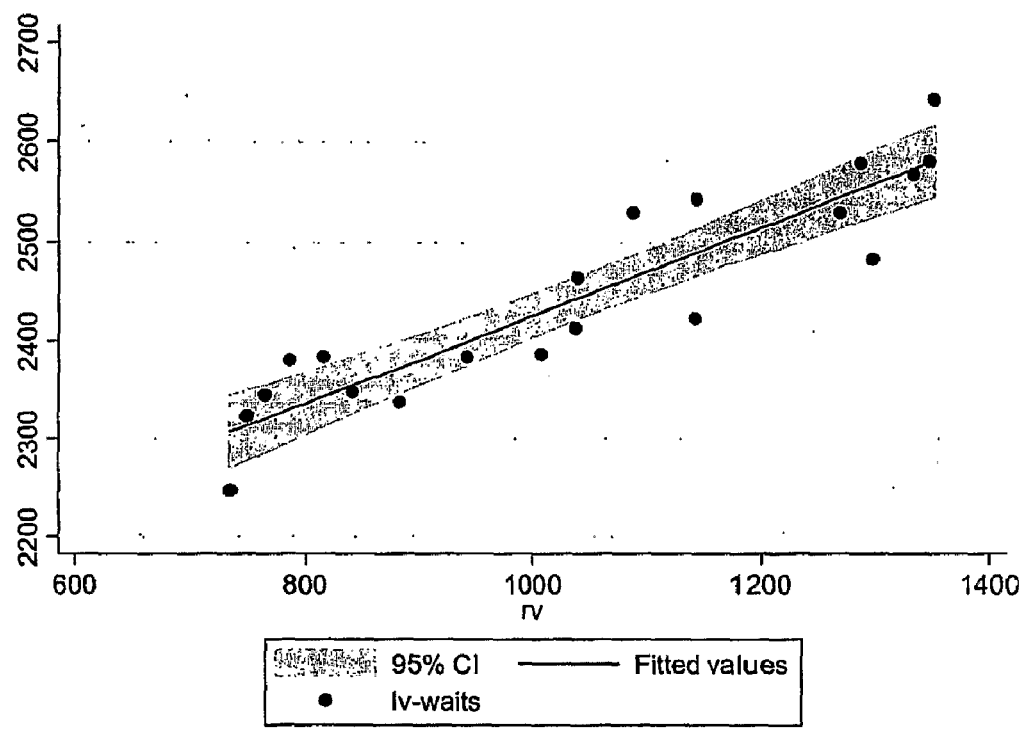
FIG. 3 shows an exemplary plot of linear regression analysis results of right and left ventricle cross-sectional areas indicating interventricular synchrony.

In Table 2, a significant linear relationship is found between RV and LV areas with the probability of having this relationship as a chance association less than 0.00001 (highly significant). In addition, the regression coefficient of 1.88 is highly significant (p<0.0001) and the coefficient of determination (labeled R-squared) is 0.84 (greater than 0.5). All of these measures indicate a linear relationship between the RV and LV areas and thus indicate interventricular synchrony. This is further shown in the regression plot of FIG. 3 showing the RV areas on the horizontal axis versus the LV areas on the vertical axis. The fitted regression line is shown with the 95% confidence interval. Note that the left ventricular areas in FIG. 3 vary closely with the right ventricular areas indicating coordinated or synchronous contractile activity of the ventricles.

In contrast, the statistical analysis in the Table 3 is representative of data obtained from a patient in which the right and left ventricular areas are not closely associated or correlated and thus do not have a significant linear relationship. In this case, the linear relationship is not significant. The value of the F statistic occurring with a chance association is 0.69 (highly probable by chance alone), The regression coefficient is 0.149 and does not differ significantly from 0 (p=0.682). The coefficient of determination is only 0.0096 (i.e., meaning that only 0.96% of the variation in left ventricular area is due to variation in right ventricular area). Therefore, there is not a significant linear relationship between the ventricular areas indicating that the ventricles do not contract in a coordinated or synchronous fashion. This is further shown in the plot of RV and LV areas of FIG. 4.

TABLE 3

| regress v49 lvboston | | | | | Number of obs = | 20 |
|---|---|---|---|---|---|---|
| | | | | | $F(1, 18) =$ | 0.17 |
| Source | ss | df | MS | | Prob > F = | 0.6816 |
| Model | 19253.9153 | 1 | 19253.9153 | | R-squared = | 0.0096 |
| Residual | 1992481.03 | 18 | 110693.391 | | Adj R-squared = | −0.0455 |
| Total | 2011734.95 | 19 | 105880.787 | | Root MSE = | 332.71 |
| v49 | Coef. | Std. Err. | t | P > |t| | [95% Conf. Interval] | |
| lvboston | .1493133 | .3580137 | 0.42 | 0.682 | −.6028457 | .9014722 |
| _cons | 1340.429 | 1252.681 | 1.07 | 0.299 | −1291.358 | 3972.215 |

Figure 4:
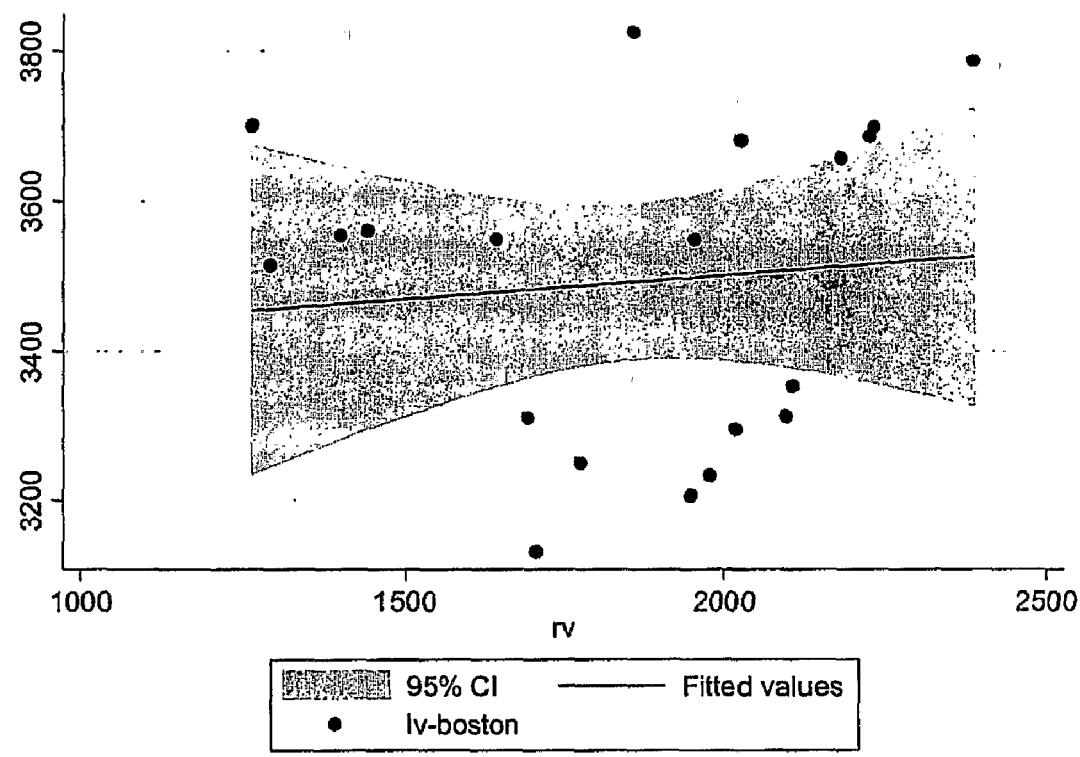
FIG. 4 shows an exemplary plot of linear regression analysis results of right and left ventricle cross-sectional areas indicating an interventricular dyssynchronous condition.

As shown in FIG. 4, there is not a significant relationship between changes in RV and LV areas indicating that the right and left ventricles are not acting in a coordinated or synchronous fashion. Accordingly, in the second example, the patient would be a candidate for biventricular pacing which has been shown to improve symptoms, as well as survival, in patients with reduced ventricular function. The patient represented in the first example would not be a candidate for this therapy given that the right and left ventricles are already functioning in a synchronous fashion without the use of biventricular pacing.

The electrocardiographic QRS width (i.e., the current standard criterion for the use of biventricular pacing) was compared to the linear regression determination of interventricular synchrony. As shown in Table 4, four patients were identified with interventricular dyssynchrony who would not have been identified by standard electrocardiographic criteria.

TABLE 4

| | Key frequency row percentage column percentage | | |
|---|---|---|---|
| 1 if dyssynchronous | 1 if qrs width ≧ to 0.12 (0 otherwise) | | |
| (0 if not) by regression | 0 | 1 | Total |
| 0 | 9 | 1 | 10 |
| | 90.00 | 10.00 | 100.00 |
| | 69.23 | 25.00 | 58.82 |
| 1 | 4 | 3 | 7 |
| | 57.14 | 42.86 | 100.00 |
| | 30.77 | 75.00 | 41.18 |
| Total | 13 | 4 | 17 |
| | 76.47 | 23.53 | 100.00 |
| | 100.00 | 100.00 | 100.00 |
| Pearson chi2(1) = 2.4706 | | Pr = 0.116 | |

Figure 5:
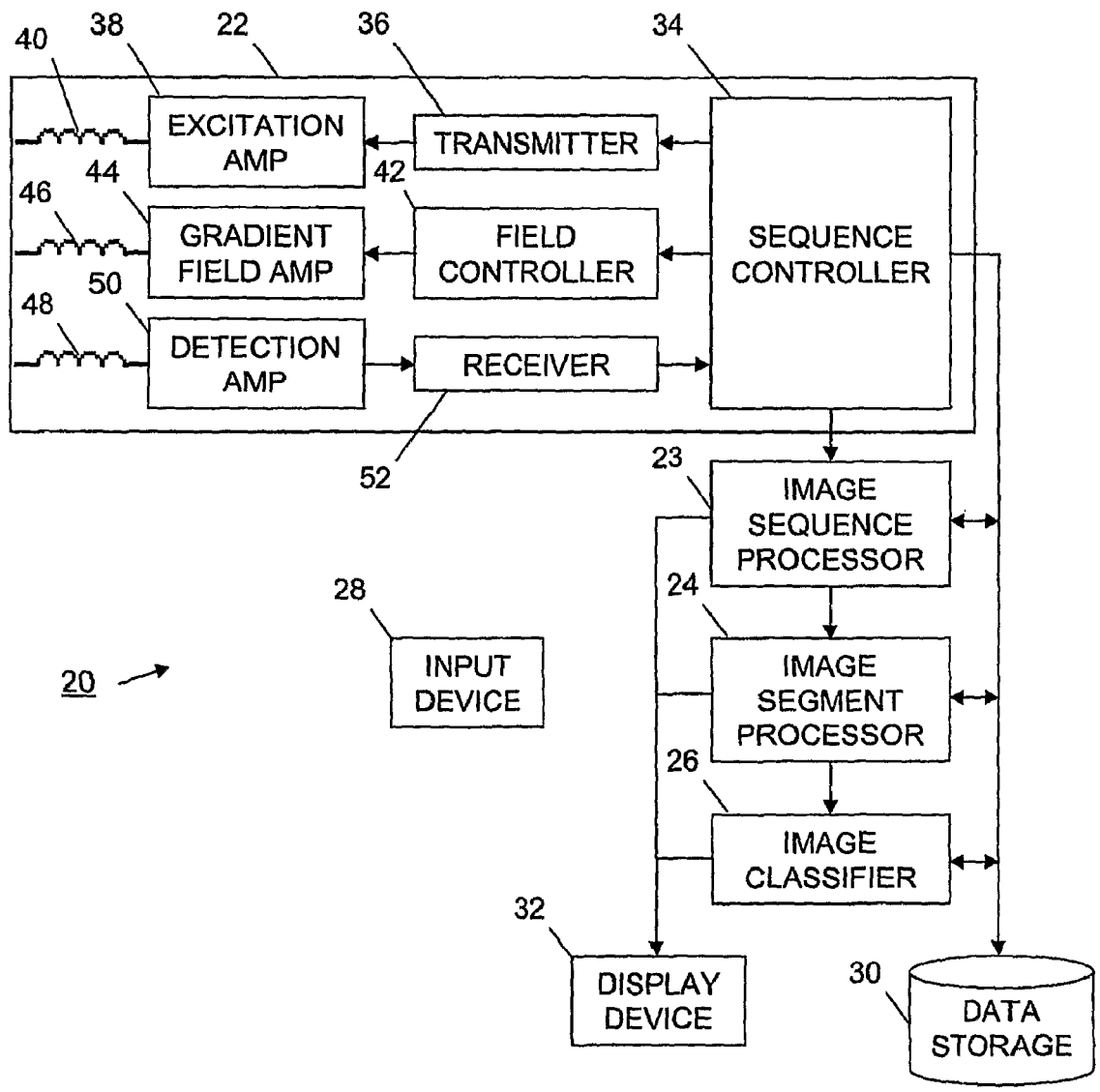
FIG. 5 is a block diagram of an exemplary embodiment of an apparatus for detecting interventricular dyssynchrony.

With reference to FIG. 5, an exemplary embodiment of an apparatus for detecting interventricular dyssynchrony may include a medical imaging system 20. The medical imaging system 20 may include an MRI device 22, an image sequence processor 23, an image segment processor 24, an image classifier 26, input device(s) 28, data storage device(s) 30, and display device(s) 32. The MRI device 22, for example, may include sequence controller(s) 34, transmitter(s) 36, excitation amplifier(s) 38, excitation coil(s) 40, field controller(s) 42, gradient field amplifier(s) 44, gradient coil(s) 46, detection coil(s) 48, detection amplifier(s) 50, and receiver(s) 52. In other embodiments, any combination of the image sequence processor 23, image segment processor 24, image classifier 26, input device(s) 28, data storage device(s) 30, and display device(s) 32 may be included with the MRI device 22 from a functional or physical standpoint.

The image segment processor 24 may segment a left ventricle and a right ventricle in each of a plurality of source images of a subject's heart to form left and right ventricle segments in a corresponding plurality of segmented images. Each source image may include at least a portion of a cross section of the subject's heart along a short axis plane. More specifically, each source image may include cross sections of the right and left ventricles of the subject's heart in common spatial relation along the short axis plane and in common temporal relation in reference to a cardiac cycle associated with the subject's heart. The plurality of source images as well as the corresponding plurality of segmented images may both be temporally-spaced in relation to the cardiac cycle.

The image classifier 26 is in operative communication with the image segment processor 24 and may determine a first cross-sectional area associated with the left ventricle segment and a second cross-sectional area associated with the right ventricle segment for each segmented image. The image classifier 26 may also compare the first and second cross-sectional areas for each segmented image and classify the subject's heart in an interventricular dyssynchronous class or a non-dyssynchronous class based at least in part on the comparing.

The image sequence processor 23 is in operative communication with the image segment processor 24 and may generate the plurality of source images of the subject's heart from image data resulting from detection of certain characteristics of the subject's heart. The MRI device 22 is in operative communication with the image sequence processor 23 and may generate the image data by detecting the characteristics of the subject's heart.

The sequence controller 34 may control various components of the MRI device 22 for detecting magnetic resonance signals from the part (i.e., area of interest) of an object (e.g., subject, patient, etc.) being imaged. For additional information on MRI sequencing, refer to Haacke et al., Magnetic Resonance Imaging: Physical Principles and Sequence Design, Wiley-Liss, $1^{st}$ edition, 1999. The contents of the Haacke document are fully incorporated herein by reference. The transmitter 36 may selectively generate a radio frequency (RF) pulse to cause resonance in the MRI device 22 via the excitation amplifier 38 and excitation coil 40. The gradient field amplifier 44 may selectively drive the gradient coil 46 in a known manner. The field controller 42 may control the magnetic field associated gradient field amplifier 44 and gradient coil 46. The receiver 52 may receive and detect magnetic resonance signals within the area of interest (i.e., focus area) via the detection coil 48 and detection amplifier 50. The image sequence processor 23 may perform image reconstruction and various calculations for presenting imaging information associated with system operation. The display device 32 may display images and information to facilitate, for example, setup and interactive operation of the MRI device 22 via the input device 28. The data storage device 30, for example, may store detected signal data and reconstructed k-space data. The data storage device 30 may also store images and statistical information generated by the image segment processor 24 and image classifier 26.

The image sequence processor 23 may be configured such that there is sufficient memory for storing measured data and reconstructed images. The memory may be sufficient to store the whole of N-dimensional measured data as well as reconstructed data. An MR image may be constructed from the image or k-space data corresponding to a predetermined plurality of applications of an MRI pulse sequence initiated by an RF pulse from the transmitter 36. The image may be updated by collecting image or k-space data from repetitive MRI pulse sequences. An MR image, for example, may be reconstructed by performing a series of Fourier transforms along a set of orthogonal directions in k-space.

As a general description, MRI is a well-known medical imaging method in which magnetic moments are excited at specific nuclear spin precession frequencies that are proportional to the magnetic field occurring within the magnet of the MRI device 22. Spin is a fundamental property of nature, such as electrical charge or mass. Precession is a rotational motion about an axis of a vector whose origin is fixed at the origin. The RF signals resulting from the precession of these spins are received typically using detection coils 48 in the MRI device 22 and are used to generate images of a volume of interest. A pulse sequence is a selected series of RF pulses and/or magnetic field gradients applied to a spin system to produce a signal representative of some property of the spin system. For example, SSFP is one type of pulse sequence that may be adapted to reduce sensitivity to magnetic field inhomogeneities. SSFP pulse sequences are generally used for fast imaging without excessive saturation of signals. SSFP pulse sequences are particularly useful for cardiac imaging applications. MRI pulse sequences that take advantage of SSFP (e.g., Siemens' "True-FISP", General Electric's (GE's) "FIESTA", and Philips' "Balanced Fast Field Echo (FFE)") can rapidly create images characterized by T2*/T1 contrast. The time constant that describes the return to equilibrium of the transverse magnetization, $M_{XY}$, is called the spin-spin relaxation time, T2. T1 governs the rate of recovery of the longitudinal magnetization. T2* is the spin-to-spin relaxation time composed of contributions from molecular interactions and inhomogeneities in the magnetic field. For additional information on MRI operation, refer to Stark et al., Magnetic Resonance Imaging, C. V. Mosby, $3^{rd}$ edition, 1999. The contents of the Stark document are fully incorporated herein by reference.

In various combinations, the image sequence processor 23, image segment processor 24, image classifier 26, input device 28, data storage device 30, and display device 32 may be provided within an operator console, a computer work station, or a computer system associated with the MRI device 22. For example, the operator console, computer work station, or computer system may be associated with the MRI device 22 in any combination and each may include one or more input devices 28, one or more data storage device 30, and one or more display devices 32. The input device(s) 28 may include any suitable input device in any suitable combination (e.g., keyboard, keypad, control panel, pointing device (e.g., mouse, touch screen, etc.)). The data storage device(s) 30 may include any suitable data storage device in any suitable combination (e.g., erasable memory devices, optical storage devices, fixed disk, removable disk, etc.). The display device(s) 32 may include any suitable combination of one or more display devices (e.g., liquid crystal display (LCD)

monitor, flat panel display, high definition (HD) display, widescreen display, cathode ray tube (CRT) monitor, alphanumeric display, numeric display, light emitting diodes (LEDs), indicator lights, etc.).

In other embodiments of an apparatus for detecting interventricular dyssynchrony, any other type of medical imaging system capable of producing short axis images of the subject's heart with cross sections of the right and left ventricles may be used in place of the medical imaging system 20 in FIG. 5. For example, the medical imaging system may include at least one of a medical radiography device, a medical tomography device, a medical sonography device, and a nuclear medicine device. More specifically, the medical imaging system may include an echo device, an MDCT device, a SPECT device, or a PET device instead of the MRI device 22 shown in FIG. 5. Any of the aspects of FIG. 5 described above may be automated, semi-automated, or manual and may be implemented through hardware, software, firmware, or combinations thereof.

Figure 6:
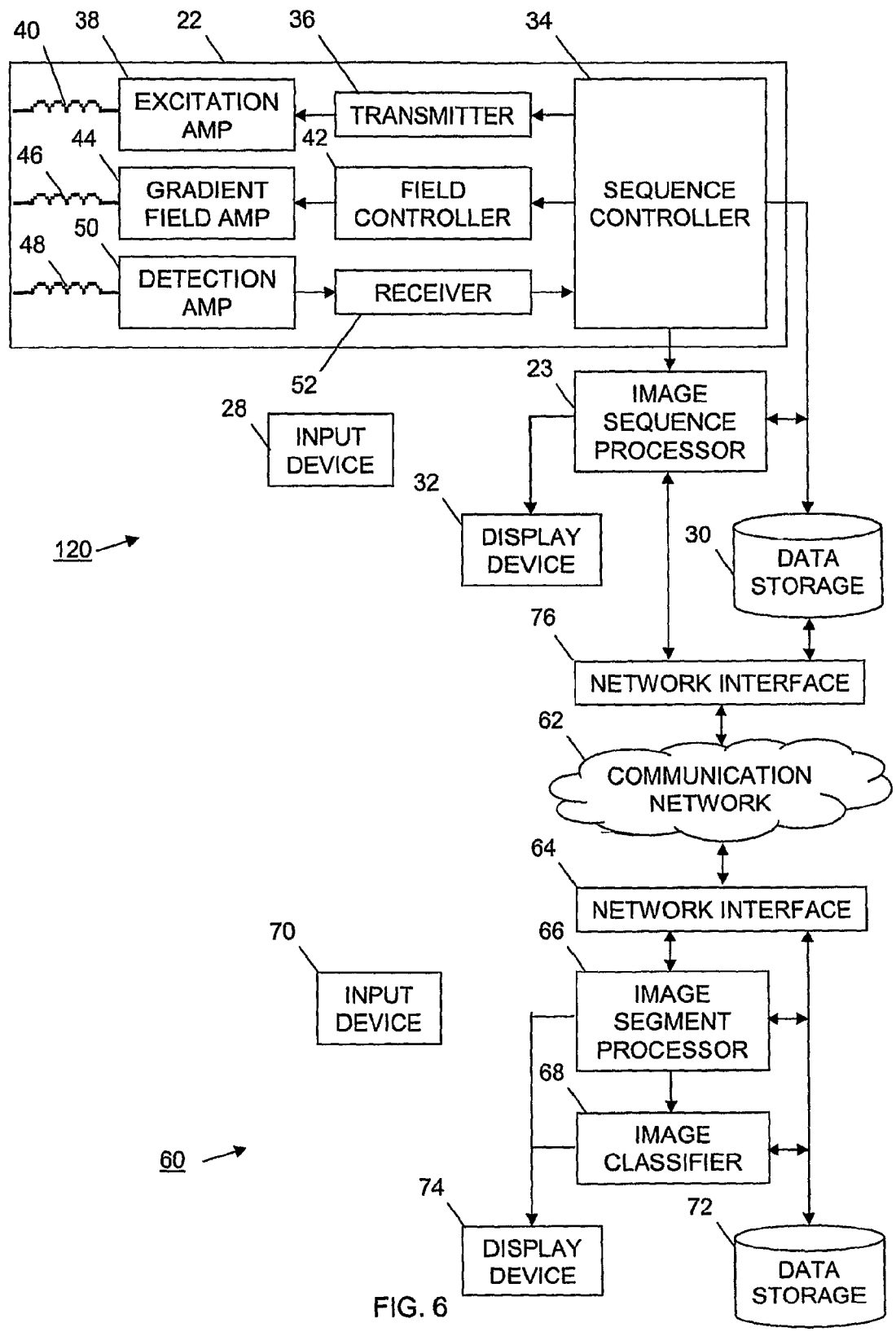
FIG. 6 is a block diagram of another exemplary embodiment of an apparatus for detecting interventricular dyssynchrony in communication with an exemplary embodiment of a medical imaging system via a communication network.

With reference to FIG. 6, another exemplary embodiment of an apparatus for detecting interventricular dyssynchrony may include a computer system 60 in communication with an exemplary embodiment of a medical imaging system 120 via a communication network 62. The computer system 60 may include a network interface 64, an image segment processor 66, an image classifier 68, input device(s) 70, data storage device(s) 72, and display device(s) 74. The medical imaging system 120 may include an MRI device 22, an image sequence processor 23, input device(s) 28, data storage device(s) 30, display device(s) 32, and a network interface 76. The MRI device 22 may include the same components and may operate in the same manner as described above for FIG. 5. Likewise, the image sequence processor 23, input device(s) 28, data storage device(s) 30, and display device(s) 32 may operate in the same manner as described above for FIG. 5. Moreover, alternatives and options provided through other embodiments of the MRI device 22, image sequence processor 23, input device(s) 28, data storage device(s) 30, and display device(s) 32 described above also apply to the medical imaging system 120 depicted in FIG. 6.

The image segment processor 66 may segment a left ventricle and a right ventricle in each of a plurality of source images of a subject's heart to form left and right ventricle segments in a corresponding plurality of segmented images. Each source image may include at least a portion of a cross section of the subject's heart along a short axis plane. More specifically, each source image may include cross sections of the right and left ventricles of the subject's heart in common spatial relation along the short axis plane and in common temporal relation in reference to a cardiac cycle associated with the subject's heart. The plurality of source images as well as the corresponding plurality of segmented images may both be temporally-spaced in relation to the cardiac cycle.

The image classifier 68 is in operative communication with the image segment processor 66 and may determine a first cross-sectional area associated with the left ventricle segment and a second cross-sectional area associated with the right ventricle segment for each segmented image. The image classifier 68 may also compare the first and second cross-sectional areas for each segmented image and classify the subject's heart in an interventricular dyssynchronous class or a non-dyssynchronous class based at least in part on the comparing.

The network interface 64 is in operative communication with the image segment processor 66 and is adapted to receive the plurality of source images from the medical imaging system 120 via the communication network 62.

The image sequence processor 23 is in operative communication with the image segment processor 66 via the network interface 64 and communication network 62. The image sequence processor 23 may generate the plurality of source images of the subject's heart from image data resulting from detection of certain characteristics of the subject's heart. The MRI device 22 is in operative communication with the image sequence processor 23 and may generate the image data by detecting the characteristics of the subject's heart.

The communication network 62 may include any combination of suitable wired and wireless communications networks (e.g., wired or wireless local area networks (LANs), wired or wireless wide area networks (WANs), the Internet, wired or wireless telephone systems (e.g., plain old telephone systems (POTS), integrated services digital networks (ISDN), cellular telephone networks, satellite telephone systems, etc.), cable television systems, satellite communication systems, etc.). The network interface 64 may be any suitable network interface compatible with the specific communication network to which it is connecting. Likewise, the network interface 76 may be any suitable network interface compatible with the specific communication network to which it is connecting. As such, the network interfaces 64, 76 need not be the same in form or function.

In other embodiments of an apparatus for detecting interventricular dyssynchrony, any other type of medical imaging system capable of producing short axis images of the subject's heart with cross sections of the right and left ventricles may be used in place of the medical imaging system 120 in FIG. 6. For example, the medical imaging system may include at least one of a medical radiography device, a medical tomography device, a medical sonography device, and a nuclear medicine device. More specifically, the medical imaging system may include an echo device, an MDCT device, a SPECT device, or a PET device instead of the MRI device 22 shown in FIG. 6. Any of the aspects of FIG. 6 described above may be automated, semi-automated, or manual and may be implemented through hardware, software, firmware, or combinations thereof.

Figure 7:
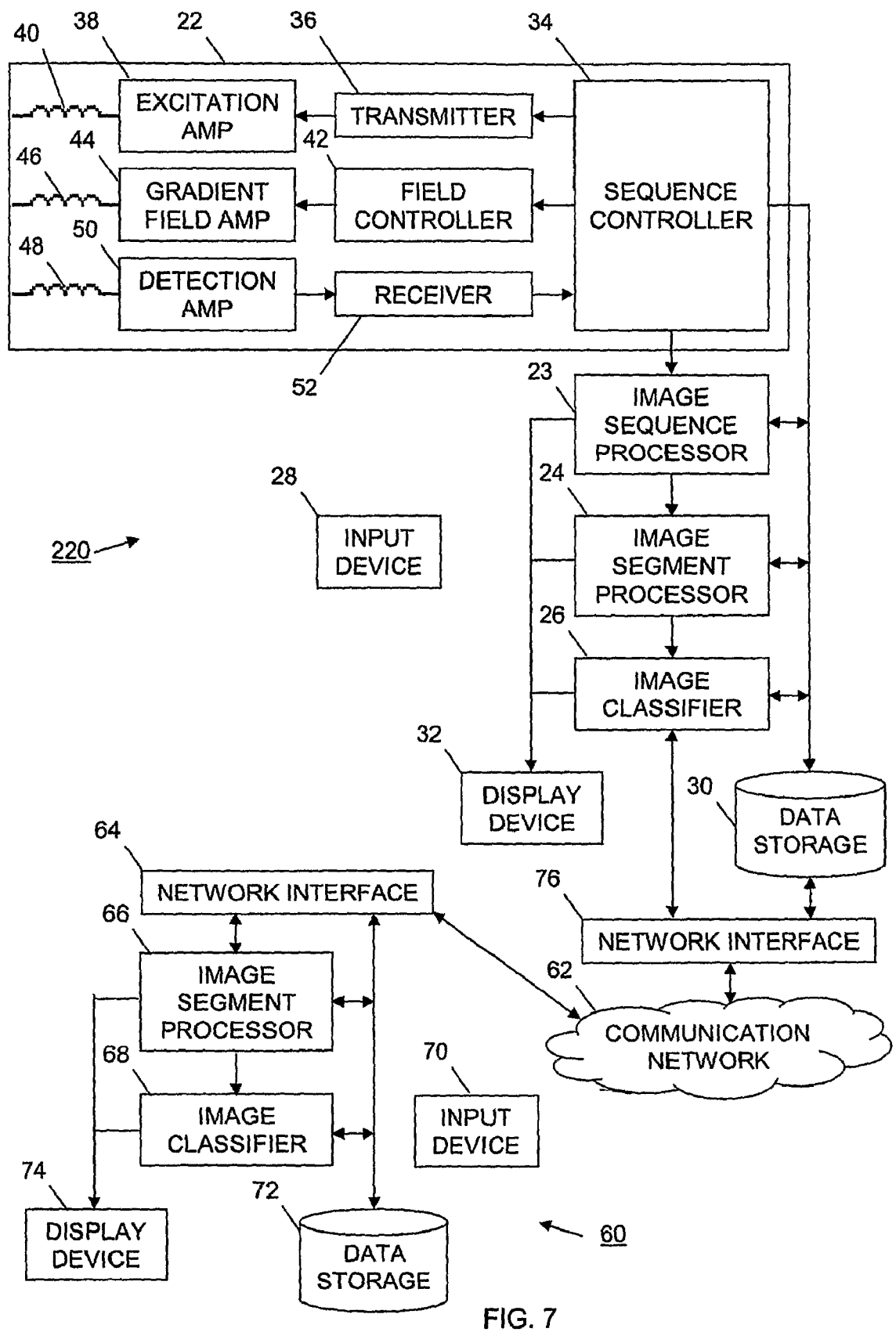
FIG. 7 is a block diagram showing the exemplary embodiment of the apparatus for detecting interventricular dyssynchrony of FIG. 6 in communication with the exemplary embodiment of the apparatus for detecting interventricular dyssynchrony of FIG. 5 via a communication network.

With reference to FIG. 7, the computer system 60 of FIG. 6 is shown in communication with a medical imaging system 220 (similar to the medical imaging system 20 of FIG. 5) via the communication network 62. The computer system 60 may include the same components and may operate in the same manner as described above for FIG. 6. Likewise, the communication network 62 may operate in the same manner as described above for FIG. 6. Moreover, alternatives and options provided through other embodiments of the computer system 60 and communication network 62 and described above also apply to the overall arrangement of equipment depicted in FIG. 7.

The medical imaging system 220 may include the MRI device 22, image sequence processor 23, image segment processor 24, image classifier 26, input device(s) 28, data storage device(s) 30, display device(s) 32, and network interface 76. The MRI device 22 may include the same components and may operate in the same maimer as described above for FIG. 5. Likewise, the image sequence processor 23, image segment processor 24, image classifier 26, input device(s) 28, data storage device(s) 30, and display device(s) 32 may operate in the same maimer as described above for FIG. 5. Additionally, the network interface 76 may operate in the same manner as described above for FIG. 6. Moreover, alternatives and options provided through other embodiments of the MRI device 22, image sequence processor 23, image segment processor 24, image classifier 26, input device(s) 28, data storage device(s) 30, display device(s) 32, and network interface 62 and described above also apply to the overall arrangement of equipment depicted in FIG. 7.

In other embodiments of an apparatus for detecting interventricular dyssynchrony, any other type of medical imaging system capable of producing short axis images of the subject's heart with cross sections of the right and left ventricles may be used in place of the medical imaging system 220 in FIG. 7. For example, the medical imaging system may include at least one of a medical radiography device, a medical tomography device, a medical sonography device, and a nuclear medicine device. More specifically, the medical imaging system may include an echo device, an MDCT device, a SPECT device, or a PET device instead of the MRI device 22 shown in FIG. 7. Any of the aspects of FIG. 7 described above may be automated, semi-automated, or manual and may be implemented through hardware, software, firmware, or combinations thereof.

Figure 8:
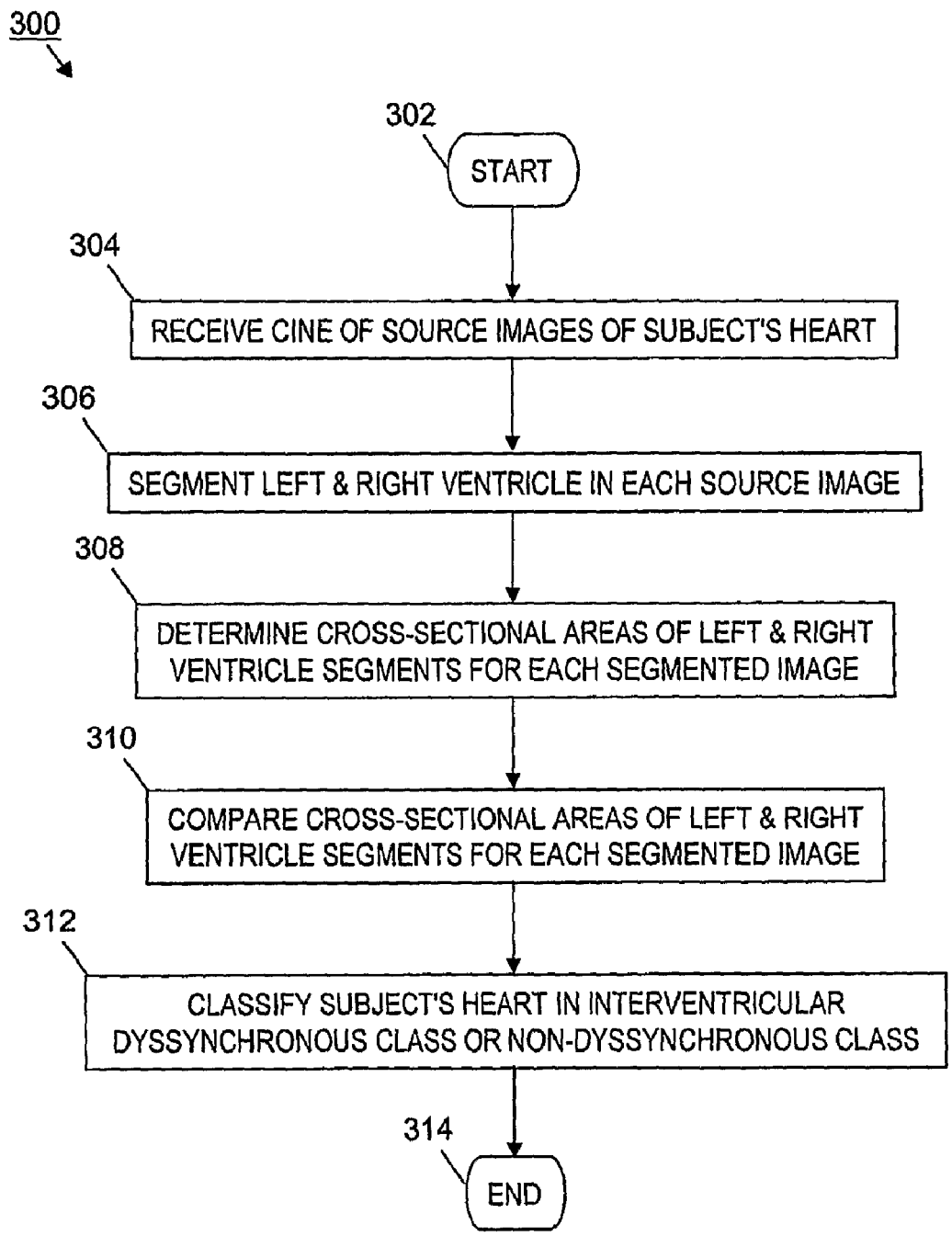
FIG. 8 is a flow chart showing an exemplary embodiment of a method of detecting interventricular dyssynchrony.

With reference to FIG. 8, an exemplary embodiment of a method 300 of detecting interventricular dyssynchrony begins at 302 where the process starts. At 304, a cine of source images of a subject's heart may be received. The cine may include a plurality of temporally-spaced source images. Each source image may include at least a portion of a cross section of the subject's heart along a short axis plane. More specifically, each source image may include cross sections of right and left ventricles of the subject's heart in common spatial relation along the short axis plane and in common temporal relation in reference to a cardiac cycle associated with the subject's heart. The plurality of source images may be temporally-spaced in relation to the cardiac cycle.

At 306, the left ventricle and the right ventricle may be individually segmented in each source image to form left and right ventricle segments in a corresponding plurality of segmented images. Next, a first cross-sectional area associated with the left ventricle segment and a second cross-sectional area associated with the right ventricle segment may be determined for each segmented image (308). At 310, the first and second cross-sectional areas may be compared for each segmented image. Next, the subject's heart may be classified in an interventricular dyssynchronous class or a non-dyssynchronous class based at least in part on the comparing (312). At 314, the process has reached its end.

In one embodiment of the method, the plurality of source images may be received from a medical imaging system via a communication network. In another embodiment, the spatial relation of the plurality of source images in the short axis plane may be associated with a mid-cavity view of the subject's heart. However, other views along the short axis plane are possible. In yet another embodiment, the segmenting in 306 may include identifying a first boundary defining the left ventricle segment and a second boundary defining the right ventricle segment in each source image. In still another embodiment, the cross-sectional area of the left ventricle segment may be determined using a first algorithm and the cross-sectional area of the right ventricle segment may be determined using a second algorithm. The first and second algorithms, for example, may include integration, geometric area approximation, or combinations thereof. For additional information on algorithms for determining cross sectional area in a bounded 2D space, refer to Seul et al., Practical Algorithms for Image Analysis: Descriptions, Examples, and Code, Cambridge University Press, 2000. The contents of the Seul document are fully incorporated herein by reference. In another embodiment, the comparing in 310 may be based at least in part on use of a linear regression model. For additional information on linear regression models, refer to Seber et al., Linear Regression Analysis, Wiley-Interscience, $2^{nd}$ edition, 2003. The contents of the Seber document are fully incorporated herein by reference.

In one embodiment, the method may also include pre-diagnosing the subject's heart as exhibiting interventricular dyssynchrony based at least in part on the classifying in 312. In another embodiment, the method may also include diagnosing the subject's heart as exhibiting interventricular dyssynchrony based at least in part on the classifying in 312 and planning treatment of the subject's heart to include implantation of a CRT device.

In one embodiment of the method, the segmenting in 306 may be based at least in part on observation of the plurality of source images by a qualified healthcare professional. In another embodiment, at least one of the determining in 308, the comparing in 310, or the classifying in 312 may be based at least in part on observation of the plurality of segmented images by a qualified healthcare professional. Any of the aspects of FIG. 8 described above may be automated, semi-automated, or manual and may be implemented through hardware, software, firmware, or combinations thereof.

Figure 9:
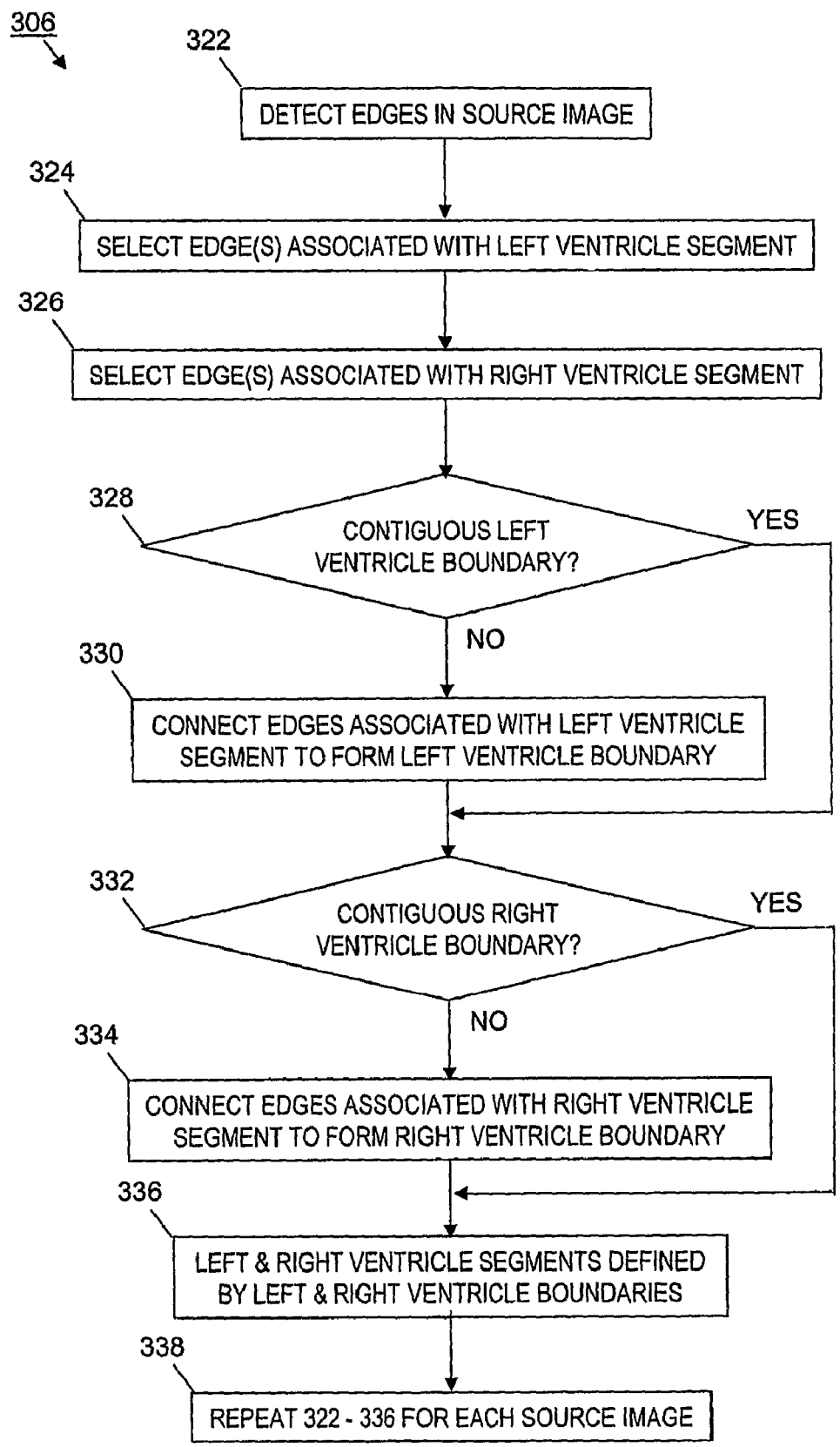
FIG. 9 is a flow chart showing an exemplary embodiment of a process for segmenting left and right ventricles from source images in relation to the method of FIG. 8.

With reference to FIG. 9, an exemplary embodiment of a process 306 for segmenting left and right ventricles from source images in relation to the method of FIG. 8 begins at 322 where edges may detected in a first source image. At 324, one or more detected edges defining at least a portion of the left ventricle segment may be selected. Next, one or more detected edges defining at least a portion of the right ventricle segment may be selected (326). Next, at 328, the process may determine if the edges selected for the left ventricle segment form a contiguous boundary. If a contiguous boundary is formed, the process advances to 332. Otherwise, at 330, the edges selected for the left ventricle segment may be connected to form a contiguous boundary.

Next, at 332, the process may determine if the edges selected for the right ventricle segment form a contiguous boundary. If a contiguous boundary is formed, the process advances to 336. Otherwise, at 334, the edges selected for the right ventricle segment may be connected to form a contiguous boundary.

Next, at 336, the left and right ventricle segments are both defined by contiguous left and right ventricle boundaries, respectively, in a first segmented image corresponding to the first source image. The operations described for 322-336 are repeated for each source image in the cine (i.e., plurality or sequence) of source images.

In one embodiment, the left ventricle boundary may be associated with an outer wall of the left ventricle. Likewise, the right ventricle boundary may be associated with an outer wall of the right ventricle. In other embodiments, the boundaries defining the left and right ventricle segments may be associated with inner walls of the ventricles, approximations of either the outer walls or inner walls, an average or approximation of the outer walls and inner walls, or some other suitable characteristic of the ventricles that defines cross-sectional areas of both ventricles over time. Any of the aspects of FIG. 9 described above may be automated, semi-automated, or manual and may be implemented through hardware, software, firmware, or combinations thereof.

Figure 10:
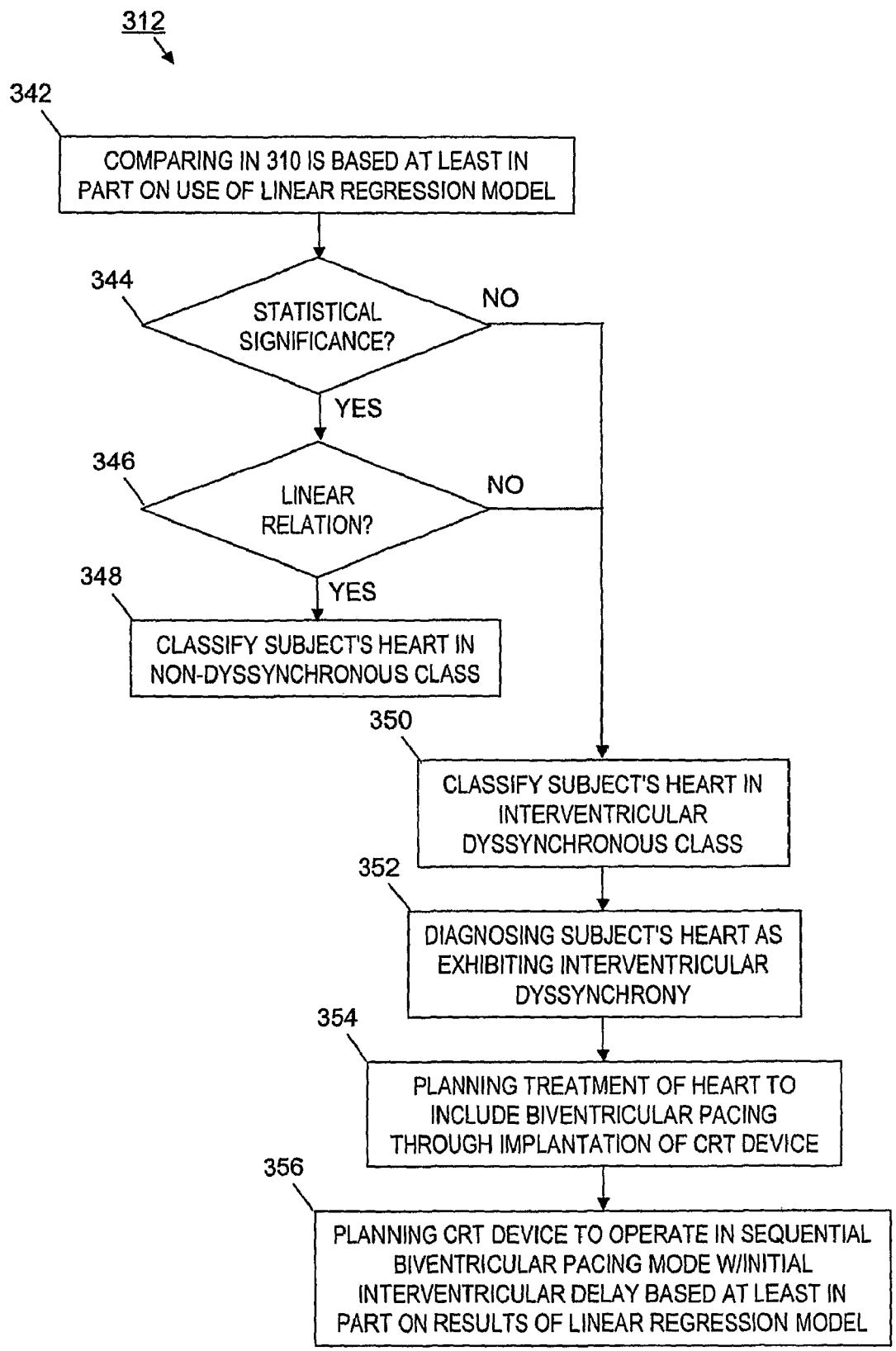
FIG. 10 is a flow chart showing an exemplary embodiment of a process for classifying a subject's heart in a non-dyssynchronous class or an interventricular dyssynchronous class in relation to the method of FIG. 8.

With reference to FIG. 10, an exemplary embodiment of a process 312 for classifying a subject's heart in a non-dyssynchronous class or an interventricular dyssynchronous class in relation to the method of FIG. 8 begins at 342 where the comparing in 310 (FIG. 8) is based at least in part on use of a linear regression model. Next, the process may determine if the linear regression model attains statistical significance (344). If statistical significance is attained, at 346, the process may determine if the linear regression model indicates there is a linear relation between the cross-sectional areas of the left and right ventricle segments over the cardiac cycle. If there is a linear relation, the subject's heart may be classified in the non-dyssynchronous class (348).

At 344, if statistical significance is not attained, the subject's heart may be classified in the interventricular dyssynchronous class (350). Similarly, at 346, if there is not a linear relation, the subject's heart may be classified in the interventricular dyssynchronous class (350). Next, the subject's heart may be diagnosed as exhibiting interventricular dyssynchrony based at least in part on the classifying (352). At 354, treatment of the subject's heart may be planned to include biventricular pacing through implantation of a CRT device. Next, the subject's CRT device may be planned to operate in a sequential biventricular pacing mode with an initial interventricular delay value based at least in part on results of the linear regression model (356). Any of the aspects of FIG. 10 described above may be automated, semi-automated, or manual and may be implemented through hardware, software, firmware, or combinations thereof.

Figure 11:
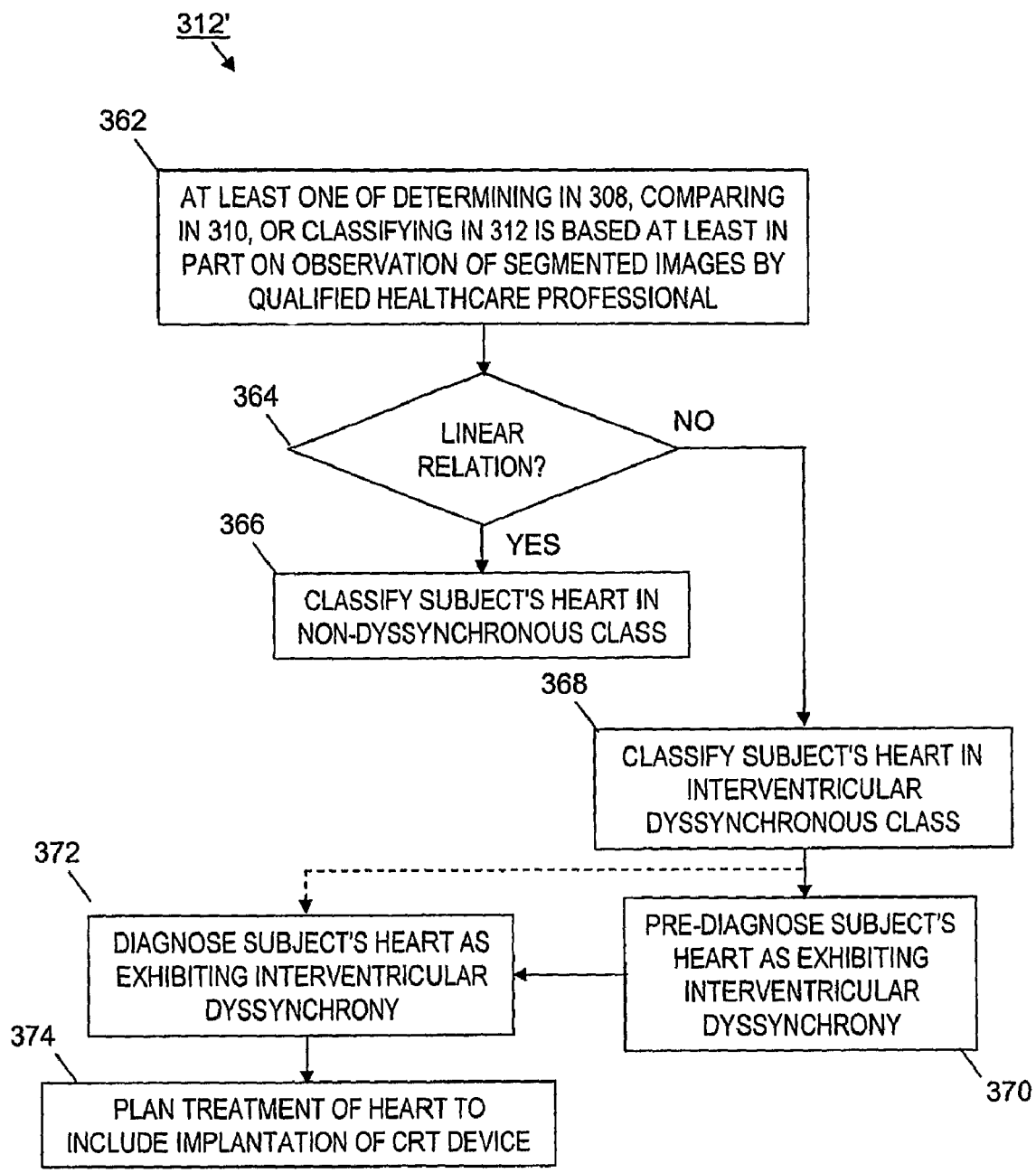
FIG. 11 is a flow chart showing another exemplary embodiment of a process for classifying a subject's heart in a non-dyssynchronous class or an interventricular dyssynchronous class in relation to the method of FIG. 8.

With reference to FIG. 11, another exemplary embodiment of a process 212 for classifying a subject's heart in a non-dyssynchronous class or an interventricular dyssynchronous class in relation to the method of FIG. 8 begins at 362 where at least one of the determining in 308 (FIG. 8), the comparing in 310 (FIG. 8), or the classifying in 312 (FIG. 8) is based at least in part on observation of the segmented images by a qualified healthcare professional. Next, at 364, the process may determine if there is a linear relation between the cross-sectional areas of the left and right ventricle segments over the cardiac cycle. If there is a linear relation, the subject's heart may be classified in the non-dyssynchronous class (366). At 364, if there is not a linear relation, the subject's heart may be classified in the interventricular dyssynchronous class (368). At 370, the subject's heart may be pre-diagnosed as exhibiting interventricular dyssynchrony based at least in part on the classifying. Next, the subject's heart may be diagnosed as exhibiting interventricular dyssynchrony based at least in part on the classifying (372). At 374, treatment of the subject's heart may be planned to include implantation of a CRT device.

In another embodiment, the process may advance from classifying the subject's heart in the interventricular dyssynchronous class in 368 to diagnosing the subject's heart with interventricular dyssynchrony in 372 without the pre-diagnosis stage. This alternate embodiment, for example, may presume there is sufficient information available to make a proper diagnosis where the pre-diagnosis stage may be used when additional considerations are planned. Any of the aspects of FIG. 11 described above may be automated, semi-automated, or manual and may be implemented through hardware, software, firmware, or combinations thereof.

Figure 12:
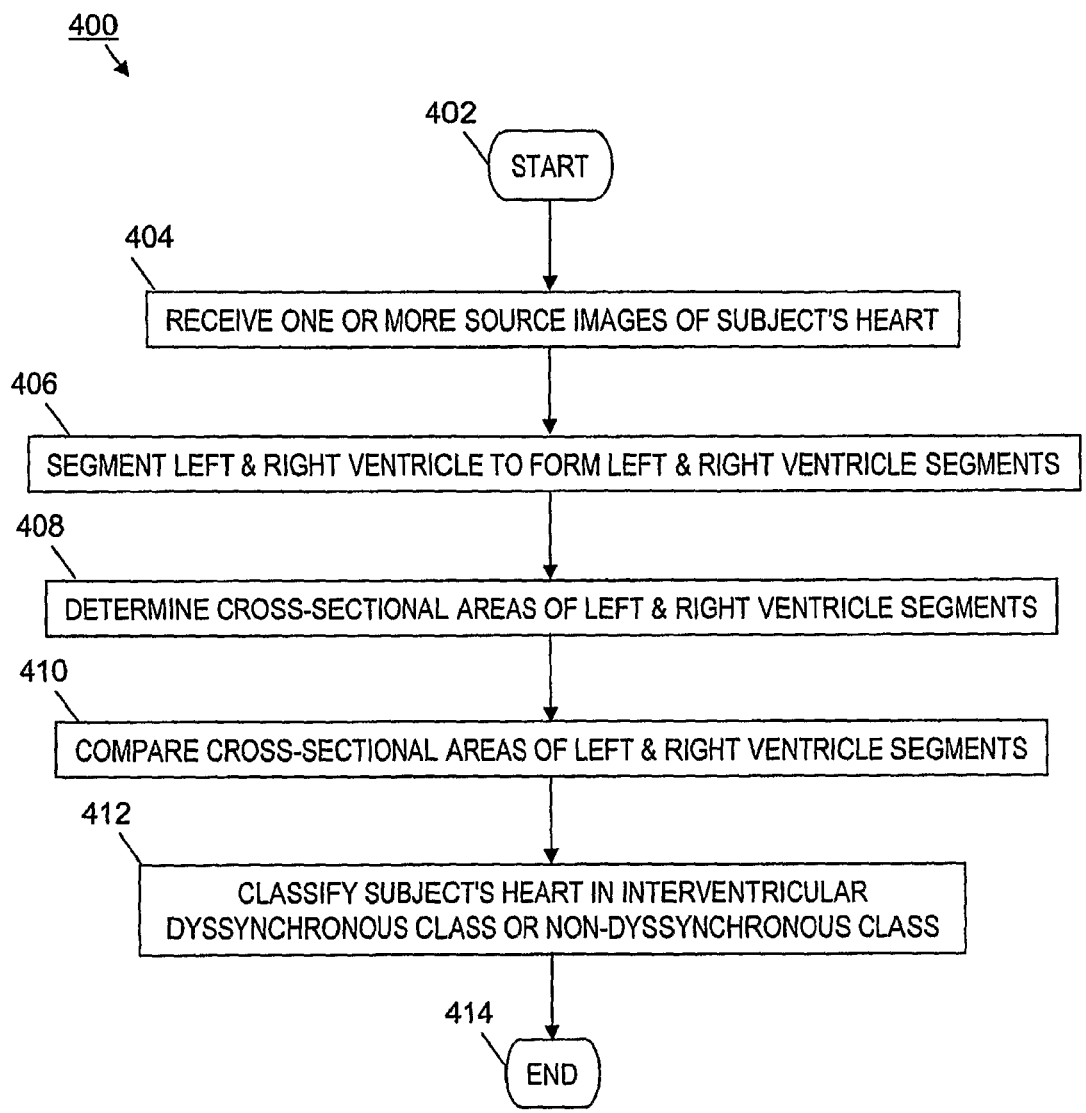
FIG. 12 is a flow chart showing another exemplary embodiment of a method of detecting interventricular dyssynchrony.

With reference to FIG. 12, another exemplary embodiment of a method 400 of detecting interventricular dyssynchrony begins at 402 where the process starts. At 404, one or more source images of a subject's heart may be received. Each source image may include at least a portion of a cross section of the subject's heart along a short axis plane. More specifically, the one or more source images, at least in combination, may include cross sections of right and left ventricles of the subject's heart in common spatial relation along the short axis plane and in common temporal relation to a cardiac cycle associated with the subject's heart.

At 406, the left ventricle and the right ventricle may be individually segmented from the one or more source images to form left and right ventricle segments in one or more segmented images. Next, a first cross-sectional area associated with the left ventricle segment and a second cross-sectional area associated with the right ventricle segment may be determined from the one or more segmented images (408). At 410, the first and second cross-sectional areas may be compared. Next, the subject's heart may be classified in an interventricular dyssynchronous class or a non-dyssynchronous class based at least in part on the comparing (412). At 414, the process has reached its end.

In one embodiment, the method may also include pre-diagnosing the subject's heart as exhibiting interventricular dyssynchrony based at least in part on the classifying in 412. In another embodiment, the method may also include diagnosing the subject's heart as exhibiting interventricular dyssynchrony based at least in part on the classifying in 412 and planning treatment of the subject's heart to include implantation of a CRT device. In yet another embodiment, at least one of the determining in 408, the comparing in 410, or the classifying in 412 may be based at least in part on observation of the segmented images by a qualified healthcare professional. Any of the aspects of FIG. 12 described above may be automated, semi-automated, or manual and may be implemented through hardware, software, firmware, or combinations thereof.

With reference to FIGS. 5-7, another embodiment of an apparatus for detecting interventricular dyssynchrony may include an image segment processor (e.g., 24, 66) and an image classifier (e.g., 26, 68). The image segment processor may individually segment a left ventricle and a right ventricle from one or more source images of a subject's heart to form left and right ventricle segments in one or more segmented images. Each source image may include at least a portion of a cross section of the subject's heart along a short axis plane. More specifically, the one or more source images, at least in combination, may include cross sections of the right and left ventricles of the subject's heart in common spatial relation along the short axis plane and in common temporal relation to a cardiac cycle associated with the subject's heart. In the embodiment being described, the image classifier is in operative communication with the image segment processor and may determine a first cross-sectional area associated with the left ventricle segment and a second cross-sectional area associated with the right ventricle segment from the left and right ventricle segments. The image classifier may also compare the first and second cross-sectional areas and classify the subject's heart in an interventricular dyssynchronous class or a non-dyssynchronous class based at least in part on the comparing.

An image sequence processor (e.g., 23) may be added to the embodiment being described such that it is in operative communication with the image segment processor. The image sequence processor may generate the source images of the subject's heart from image data resulting from detection of certain characteristics of the subject's heart. A medical imaging device (e.g., 22) may also be added to the embodiment being described such that it is in operative communication with the image sequence processor. The medical imaging device may generate the image data by detecting the characteristics of the subject's heart. A network interface (e.g., 64) may be added to the embodiment being described such that it is in operative communication with the image segment processor. The network interface may be adapted to receive the source images from a medical imaging system via a communication network (e.g., 62).

While the invention is described herein in conjunction with one or more exemplary embodiments, it is evident that many alternatives, modifications, and variations will be apparent to those skilled in the art. For example, the method and apparatus for detecting interventricular dyssynchrony may be used in conjunction with a variety of medical imaging modalities. Accordingly, exemplary embodiments in the preceding description are intended to be illustrative, rather than limiting, of the spirit and scope of the invention. More specifically, it is intended that the invention embrace all alternatives, modifications, and variations of the exemplary embodiments described herein that fall within the spirit and scope of the appended claims or the equivalents thereof. Any element in a claim that does not explicitly state "means for" performing a specified function, or "step for" performing a specific function, is not to be interpreted as a "means" or "step" clause as specified in 35 U.S.C. §112, ¶6. In particular, the use of "step of" in the claims herein is not intended to invoke the provisions of 35 U.S.C. §112, ¶6.

The invention claimed is:

1. An apparatus for detecting interventricular dyssynchrony, including:
   an image segment processor segmenting a left ventricle and a right ventricle in each of a plurality of source images of a heart to form left and right ventricle segments in a corresponding plurality of segmented images, each source image including at least a portion of a cross section of the heart along a short axis plane, each source image including cross sections of the right and left ventricles of the heart in common spatial relation along the short axis plane and in common temporal relation in reference to a cardiac cycle associated with the heart, the plurality of source images and corresponding plurality of segmented images being temporally-spaced in relation to the cardiac cycle; and
   an image classifier, in operative communication with the image segment processor, determining a first cross-sectional area associated with the left ventricle segment and a second cross-sectional area associated with the right ventricle segment for each segmented image, comparing, at least in part based on use of a linear regression model, the first and second cross-sectional areas for each segmented image, and classifying the heart in an interventricular dyssynchronous class or a non-dyssynchronous class, based at least in part on the comparing, by classifying the heart in the non-dyssynchronous class if the linear regression model attains statistical significance and indicates a linear relation between the first and second cross-sectional areas over the cardiac cycle and by classifying the heart in the interventricular dyssynchronous class if the linear regression model indicates there is not a linear relation between the first and second cross-sectional areas over the cardiac cycle.

2. The apparatus of claim 1, further including:
   an image sequence processor, in operative communication with the image segment processor, generating the plurality of source images of the heart from image data resulting from detecting characteristics of the heart.

3. The apparatus of claim 2, further including:
   a medical imaging device, in operative communication with the image sequence processor, generating the image data by detecting the characteristics of the heart.

4. The apparatus of claim 3 wherein the medical imaging device includes at least one of a medical radiography device, a medical tomography device, a medical sonography device, and a nuclear medicine device.

5. The apparatus of claim 4 wherein the medical imaging device includes a magnetic resonance imaging device, an echocardiography device, a multi-detector computed tomography device, a single photon emission computed tomography device, or a positron emission tomography device.

6. The apparatus of claim 1, further including:
   a network interface, in operative communication with the image segment processor, adapted to receive the plurality of source images from a medical imaging system via a communication network.

7. A method of detecting interventricular dyssynchrony, including:
   a) receiving a plurality of source images of a heart, each source image including at least a portion of a cross section of the heart along a short axis plane, each source image including cross sections of right and left ventricles of the heart in common spatial relation along the short axis plane and in common temporal relation in reference to a cardiac cycle associated with the heart, the plurality of source images being temporally-spaced in relation to the cardiac cycle;
   b) segmenting the left ventricle and the right ventricle in each source image to form left and right ventricle segments in a corresponding plurality of segmented images;
   c) determining a first cross-sectional area associated with the left ventricle segment and a second cross-sectional area associated with the right ventricle segment for each segmented image;
   d) comparing, at least in part based on use of a linear regression model, the first and second cross-sectional areas for each segmented image;
   e) classifying the heart in an interventricular dyssynchronous class or a non-dyssynchronous class based at least in part on the comparing, the classifying including:
   f) classifying the heart in the non-dyssynchronous class if the linear regression model attains statistical significance and indicates a linear relation between the first and second cross-sectional areas over the cardiac cycle; and
   g) classifying the heart in the interventricular dyssynchronous class if the linear regression model indicates there is not a linear relation between the first and second cross-sectional areas over the cardiac cycle.

8. The method of claim 7 wherein the plurality of source images are received from a medical imaging system via a communication network.

9. The method of claim 7 wherein the spatial relation of the plurality of source images in the short axis plane is associated with a mid-cavity view of the heart.

10. The method of claim 7, further including:
    h) identifying a first boundary defining the left ventricle segment and a second boundary defining the right ventricle segment in each source image.

11. The method of claim 10, further including:
    i) detecting edges in each source image;
    j) in each source image, selecting one or more detected edges defining at least a portion of the left ventricle segment; and
    k) in each source image, selecting one or more detected edges defining at least a portion of the right ventricle segment.

12. The method of claim 11, further including:
    l) in each source image, connecting the detected edges defining at least a portion of the left ventricle segment to form the first boundary; and
    m) in each source image, connecting the detected edges defining at least a portion of the right ventricle segment to form the second boundary.

13. The method of claim 10 wherein the first boundary is associated with an outer wall of the left ventricle and the second boundary is associated with an outer wall of the right ventricle.

14. The method of claim 7 wherein the first cross-sectional area is determined using a first algorithm and the second cross-sectional area is determined using a second algorithm.

15. The method of claim 7, further including:
   h) diagnosing the heart as exhibiting interventricular dyssynchrony based at least in part on the classifying; and
   i) planning treatment of the heart to include biventricular pacing through implantation of a cardiac resynchronization therapy device.

16. The method of claim 15, further including:
   j) planning for the cardiac resynchronization therapy device to operate in a sequential biventricular pacing mode with an initial interventricular delay value based at least in part on results of the linear regression model.

17. The method of claim 7, further including:
   h) classifying the heart in the interventricular dyssynchronous class if results of the linear regression model fail to attain statistical significance.

18. The method of claim 7, further including:
   h) pre-diagnosing the heart as exhibiting interventricular dyssynchrony based at least in part on the classifying.

19. The method of claim 7, further including:
   h) diagnosing the heart as exhibiting interventricular dyssynchrony based at least in part on the classifying; and
   i) planning treatment of the heart to include implantation of a cardiac resynchronization therapy device.

20. The method of claim 7 wherein the segmenting in b) is based at least in part on observation of the plurality of source images by a qualified healthcare professional.

21. The method of claim 7 wherein at least one of the determining in c), comparing in d), and classifying in at least one of e), f), and g) is based at least in part on observation of the plurality of segmented images by a qualified healthcare professional.

22. The method of claim 21, further including:
   h) pre-diagnosing the heart as exhibiting interventricular dyssynchrony based at least in part on the classifying.

23. The method of claim 21, further including:
   h) diagnosing the heart as exhibiting interventricular dyssynchrony based at least in part on the classifying;
   i) planning treatment of the heart to include implantation of a cardiac resynchronization therapy device.

24. A method of detecting interventricular dyssynchrony, including:
   a) receiving one or more source images of a heart, each source image including at least a portion of a cross section of the heart along a short axis plane, the one or more source images including cross sections of right and left ventricles of the heart in common spatial relation along the short axis plane and in common temporal relation to a cardiac cycle associated with the heart;
   b) segmenting the left ventricle and the right ventricle from the one or more source images to form left and right ventricle segments in one or more segmented images;
   c) determining a first cross-sectional area associated with the left ventricle segment and a second cross-sectional area associated with the right ventricle segment from the one or more segmented images;
   d) comparing, at least in part based on use of a linear regression model, the first and second cross-sectional areas; and
   e) classifying the heart in an interventricular dyssynchronous class or a non-dyssynchronous class based at least in part on the comparing, the classifying including:
   f) classifying the heart in the non-dyssynchronous class if the linear regression model attains statistical significance and indicates a linear relation between the first and second cross-sectional areas over the cardiac cycle; and
   g) classifying the heart in the interventricular dyssynchronous class if the linear regression model indicates there is not a linear relation between the first and second cross-sectional areas over the cardiac cycle.

25. The method of claim 24, further including:
   h) pre-diagnosing the heart as exhibiting interventricular dyssynchrony based at least in part on the classifying.

26. The method of claim 24, further including:
   h) diagnosing the heart as exhibiting interventricular dyssynchrony based at least in part on the classifying;
   i) planning treatment of the heart to include implantation of a cardiac resynchronization therapy device.

27. The method of claim 24 wherein at least one of the determining in c), comparing in d), or classifying in at least one of e), f), and g) is based at least in part on observation of the segmented images by a qualified healthcare professional.

28. An apparatus for detecting interventricular dyssynchrony, including:
   an image segment processor segmenting a left ventricle and a right ventricle from one or more source images of a heart to form left and right ventricle segments in one or more segmented images, each source image including at least a portion of a cross section of the heart along a short axis plane, the one or more source images, at least in combination, including cross sections of right and left ventricles of the heart in common spatial relation along the short axis plane and in common temporal relation in reference to a cardiac cycle associated with the heart; and
   an image classifier, in operative communication with the image segment processor, determining a first cross-sectional area associated with the left ventricle segment and a second cross-sectional area associated with the right ventricle segment, comparing, at least in part based on use of a linear regression model, the first and second cross-sectional areas, and classifying the heart in an interventricular dyssynchronous class or a non-dyssynchronous class based at least in part on the comparing, by classifying the heart in the non-dyssynchronous class if the linear regression model attains statistical significance and indicates a linear relation between the first and second cross-sectional areas over the cardiac cycle and by classifying the heart in the interventricular dyssynchronous class if the linear regression model indicates there is not a linear relation between the first and second cross-sectional areas over the cardiac cycle.

29. The apparatus of claim 28, further including:
   an image sequence processor, in operative communication with the image segment processor, generating the one or more source images of the heart from image data resulting from detecting characteristics of the heart.

30. The apparatus of claim 29, further including:
   a medical imaging device, in operative communication with the image sequence processor, generating the image data by detecting the characteristics of the heart.

31. The apparatus of claim 28, further including:
   a network interface, in operative communication with the image segment processor, adapted to receive the one or more source images from a medical imaging system via a communication network.

* * * * *